US008784929B2

(12) United States Patent
Wallace et al.

(10) Patent No.: US 8,784,929 B2
(45) Date of Patent: Jul. 22, 2014

(54) BILAYERS

(71) Applicant: Isis Innovation Limited, Oxford (GB)

(72) Inventors: Mark Ian Wallace, Oxford (GB);
Andrew John Heron, Oxford (GB);
Matthew Alexander Holden, Amherst, MA (US)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 13/652,481

(22) Filed: Oct. 16, 2012

(65) Prior Publication Data

US 2013/0129910 A1 May 23, 2013

Related U.S. Application Data

(63) Continuation of application No. 12/733,275, filed as application No. PCT/GB2008/002805 on Aug. 19, 2008, now abandoned.

(30) Foreign Application Priority Data

Aug. 21, 2007 (GB) .................................. 0716264.7

(51) Int. Cl.
*G01N 33/92* (2006.01)
*G01N 33/53* (2006.01)

(52) U.S. Cl.
USPC ................ 427/2.1; 435/7.1; 435/7.2; 436/71; 436/86

(58) Field of Classification Search
None
See application file for complete search history.

(56) References Cited

FOREIGN PATENT DOCUMENTS

| WO | WO 02/072873 | 9/2002 |
|---|---|---|
| WO | WO 2006/100484 | 9/2006 |
| WO | WO 2006/110350 | 10/2006 |
| WO | WO 2006/122566 | 11/2006 |
| WO | WO 2007/013493 | 2/2007 |
| WO | WO 2007/030019 | 3/2007 |
| WO | WO 2008/012552 | 1/2008 |

OTHER PUBLICATIONS

Ide et al. An Artificial Lipid Bilayer Formed on an Agarose-Coated Glass for Simultaneous Electrical and Optical Measurement of Single Ion Channels. Biochemical and Biophysical Research Communications 265, 595-599 (1999).*
Tsofina. Production of Biomolecular Protein-Lipid Membranes in Aqueous Solution. Nature Publishing vol. 212 (1966) pp. 681-683.*
Holden et al. Functional Bionetworks from Nanoliter Water Droplets. J. Am. Chem. Soc. 9 vol. 129, No. 27, 2007 pp. 8650-8655.*
Funakoshi et al. Lipid Bilayer Formation by Contacting Monolayers in a Microfluidic Device for Membrane Protein Analysis. Anal. Chem. 2006, 78, 8169-8174.*
Funakoshi et al., "Lipid Bilayer Formation by Contacting Monolayers in a Microfluidic Device for Membrane Protein Analysis," *Analytical Chemistry*, vol. 78, pp. 8169-8174, 2006.
Heron et al., "Direct Detection of Membrane Channels from Gels Using Water-in-Oil Droplet Bilayers," *J. Am. Chem. Soc.*, vol. 129, pp. 16042-16047, 2007.

(Continued)

*Primary Examiner* — Cachet Sellman
(74) *Attorney, Agent, or Firm* — Klarquist Sparkman, LLP

(57) ABSTRACT

A method for producing a bilayer of amphipathic molecules comprising providing a hydrated support and providing a hydrophilic body, and bringing the hydrated support and hydrophilic body into contact to form a bilayer of amphipathic molecules. A bilayer produced by the method of the invention, and uses of the bilayer.

21 Claims, 16 Drawing Sheets

(56) References Cited

OTHER PUBLICATIONS

Holden et al., "Direct Introduction of Single Protein Channels and Pores into Lipid Bilayers," *J. Am. Chem. Soc.,* vol. 127, pp. 6502-6503, 2005.

Holden et al., "Functional Bionetworks from Nanoliter Water Droplets," *J. Am. Chem. Soc.,* vol. 129, pp. 8650-8655, 2007.

Ide et al., "A Novel Method for Artificial Lipid-Bilayer Formation," *Biosensors and Bioelectronics,* vol. 21, pp. 672-677, 2005.

UK Intellectual Property Office Search Report, App. No. GB0716264.7, dated Mar. 3, 2008, 1 page.

Thompson et al., "Enhanced Stability and Fluidity in Droplet on Hydrogel Bilayers for Measuring Membrane Protein Diffusion," *Nano Lett.,* vol. 7, No. 12, pp. 3875-3878, 2007.

Ziegler et al., "Agar-Supported Lipid Bilayers—Basic Structures for Biosensor Design. Electrical and Mechanical Properties," *Colloids Surfaces A: Physicochem. Eng. Aspects,* vol. 140, pp. 357-367, 1998.

\* cited by examiner

US 8,784,929 B2

BILAYERS

CROSS REFERENCE TO RELATED APPLICATIONS

This application claims priority as a CONTINUATION of prior application U.S. patent application Ser. No. 12/733,275, filed Nov. 4, 2010, PCT patent application number PCT/GB2008/002805, filed Aug. 19, 2008, and application No. GB 0716264.7, filed Aug. 21, 2007 (Paris Convention) under 35 USC 119, the disclosure for which priority is claimed and incorporated herein in its entirety by reference.

STATEMENT REGARDING GOVERNMENT SPONSORED RESEARCH

Aspects of this work were supported by Grant No. FA9550-06-C-0006 awarded by USAF/AFOSR. The government has certain rights in the subject matter.

FIELD

The present invention relates to a bilayer, such as a lipid bilayer, to a method of producing a bilayer, to the use of a bilayer and to apparatus to produce and/or use a bilayer.

BACKGROUND

Artificial planar lipid bilayers serve as simplified models of biological membranes and are widely used for the electrical characterisation of ion-channels and protein pores. Ion-channels are a diverse group of membrane proteins that selectively control the movement of specific ions across cell membranes, establishing voltage and electrochemical gradients that are fundamental to a wide variety of biological processes. In humans, ion-channels regulate everything from heartbeat and muscle contraction to hormone secretion and the release of neurotransmitters. Defective ion channel function is implicated in a growing list of disorders, including cardiac arrhythmia, periodic paralysis, epilepsy and diabetes (Ashcroft, F. M. 2000, *Academic Press*, San Diego; Ashcroft, F. M. 2006, *Nature* 440, 440-447; Kass, R. S. 2005, *Journal of Clinical Investigation* 115, 1986-1989). Protein pores are non-specific channels that allow molecules to pass across cell membranes. Protein pores can be exploited for many applications such as molecular sensing (Bayley, H. et al., 2000, *Advanced Materials* 12, 139-142; Bayley, H. & Cremer, P. S. 2001. *Nature* 413, 226-230) and DNA sequencing (Kasianowicz, J. J. et al., 1996. *Proceedings of the National Academy of Sciences of the United States of America* 93, 13770-13773; Howorka, S. et al., 2001. *Nature Biotechnology* 19, 636-639; Astier, Y. 2006. *Journal of the American Chemical Society* 128, 1705-1710).

Single-channel recording (SCR) of individual proteins is a powerful means of studying channel protein function (Sakmann, B. & Neher, E. 1995. Plenum Press, New York; London). Single-channel recording measures changes in ion-current through single protein channels, and can examine voltage dependence, gating behaviour, ligand binding affinity, and ion selectivity at the single-molecule level. Consequently, single-channel recording can help determine the molecular basis of an ion-channel disease. It is also an important technique for the development of new drugs specifically targeting channelopathies, and for screening other medicines for unwanted side-effects (Ashcroft, F. M. 2006. *Nature* 440, 440-447; Roden, D. M. 2004. *New England Journal of Medi-cine* 350, 1013-1022). Advances in these areas require much higher throughput assays of ion-channel behaviour than are currently available.

Single-channel recording typically uses either patch-clamping (Sakmann, B. & Neher, E. 1984. *Annual Review of Physiology* 46, 455-472) or artificial planar lipid bilayers (Mueller, P. et al., 1962. *Nature* 194, 979-980; White, S. H. 1986. ed. Miller, C. Plenum Press: New York). Although other methods may also be used, including excised-patch, tip-dip and on-chip methods.

Patch-clamping of whole cells is a versatile and sensitive means of examining channels, but is time-consuming and often complicated by the heterogeneous nature of cell membranes. In contrast, artificial planar lipid bilayers control the constituents of the system and can be used to study purified proteins. Planar lipid bilayers are usually formed either by painting, where a solution of lipid in an organic solvent is directly applied to an aperture separating two aqueous compartments (Mueller, P. et al., 1962. *Nature* 194, 979-980; White, S. H. 1986. ed. Miller, C. Plenum Press: New York), or variants of the Langmuir-Blodgett technique, where two air/water monolayers are raised past an aperture (Montal, M. & Mueller, P. 1972. *Proceedings of the National Academy of Sciences of the United States of America* 69, 3561-3566). Although widely used, planar lipid bilayers are difficult to prepare, and their short lifetime prohibits their use in many situations.

Alternative emulsion-based approaches to forming bilayers have also been proposed (Tsofina, L. M. et al., 1966. *Nature* 212, 681-683), where bilayers are created between aqueous surfaces immersed in a solution of lipid in oil. When immersed in an immiscible lipid/oil solution, aqueous surfaces spontaneously self-assemble a lipid monolayer (Cevc, G. 1993. *Phospholipids handbook*, ed. Cevc, G., Marcel Dekker, New York); Seddon, J. M. & Templer, R. H. 1995. eds. Lipowsky, R. & Sackmann, E., Elsevier, Amsterdam, Oxford), and when monolayers from two aqueous components are brought into contact they can 'zip' together to form a lipid bilayer (Tien, H. T. 1974. M. Dekker, New York; Fujiwara, H. et al., 2003. *Journal of Chemical Physics* 119, 6768-6775). Recent studies have shown that microfluidic flows (Malmstadt, N. et al., 2006. *Nano Letters* 6, 1961-1965; Funakoshi, K. et al., 2006. *Analytical Chemistry* 78, 8169-8174) and droplets (Funakoshi, K. et al., 2006. *Analytical Chemistry* 78, 8169-8174; Holden, M. A. et al., 2007. *Journal of the American Chemical Society* p 8650-5) can be contacted in a lipid/oil solution to create bilayers suitable for single-channel recording experiments.

DETAILED DESCRIPTION

According to a first aspect of the invention there is provided a method for producing a bilayer of amphipathic molecules comprising the steps of:
  (i) providing a hydrated support in a hydrophobic medium, wherein the hydrophobic medium contains amphipathic molecules and a first monolayer of amphipathic molecules is present on the surface of the hydrated support;
  (ii) providing a hydrophilic body in a hydrophobic medium, wherein the hydrophobic medium contains amphipathic molecules and a second monolayer of amphipathic molecules is present on the surface of the hydrophilic body; and
  (iii) bringing the first monolayer and the second monolayer into contact to form a bilayer of amphipathic molecules.

Preferably step (i) of the first method of the invention comprises providing a hydrated support in a hydrophobic medium, wherein the hydrophobic medium contains amphipathic molecules, and then forming a first monolayer of amphipathic molecules on the surface of the hydrated support.

Preferably step (ii) of the first method of the invention comprises providing a hydrophilic body in a hydrophobic medium, wherein the hydrophobic medium contains amphipathic molecules, and then forming a second monolayer of amphipathic molecules on the surface of the hydrophilic body.

According to a second aspect of the invention there is provided a method for producing a bilayer of amphipathic molecules comprising the steps of:
(i) providing a hydrated support containing amphipathic molecules in a hydrophobic medium, wherein a first monolayer of amphipathic molecules is present on the surface of the hydrated support;
(ii) providing a hydrophilic body containing amphipathic molecules in a hydrophobic medium, wherein a second monolayer of amphipathic molecules is present on the surface of the hydrophilic body; and
(iii) bringing the first monolayer and the second monolayer into contact to form a bilayer of amphipathic molecules.

Preferably step (i) of the second method of the invention comprises providing a hydrated support containing amphipathic molecules in a hydrophobic medium, and then forming a first monolayer of amphipathic molecules on the surface of the hydrated support.

Preferably step (ii) of the second method of the invention comprises providing a hydrophilic body containing amphipathic molecules in a hydrophobic medium, and then forming a second monolayer of amphipathic molecules on the surface of the hydrophilic body.

It is found that the method of both the first and the second aspect of the invention spontaneously forms a bilayer of amphipathic molecules which has the added advantage that it is stable over long periods of time and when subjected to environmental and/or physical stress.

The life-time of the bilayer of amphipathic molecules made according to any method of the invention may be greater than about 1 hour, 5 hours, 10 hours, 24 hours, 2 days, 1 week, 1 month, 2 months, 3 months or more.

Preferably the method of the invention forms bilayers with at least about 90% efficiency, more preferably with about 95%, 98% or 99% efficiency.

Preferably the bilayers form within 1 minute of contact between the monolayer on the hydrated support and the monolayer on hydrophilic body.

The bilayer of amphipathic molecules may be capable of withstanding physical shock, for example, the bilayer may be stable after being dropped one or more times from heights greater than 0.5 meters or 1 meter. This bilayer stability makes bilayers produced by any method of the invention easier to work with than bilayers produced by known conventional methods.

The surprisingly long life-time and stability of the bilayer of amphipathic molecules produced by any method of the invention has the benefit that a user is able to set up the bilayer and use it in long term and/or multiple experiments. It also has the benefit of being capable of being more readily used in a portable device, for example outside of a controlled laboratory environment, where the physical environment is less controllable or predictable, than conventional bilayers.

Preferably a monolayer of amphipathic molecules self assembles on the hydrated support and the hydrophilic body when each is placed in a hydrophobic medium containing amphipathic molecules.

The orientation of the amphipathic molecules in the monolayers means that a bilayer forms when the monolayers are brought into contact.

Amphipathic molecules have both a hydrophilic group and a hydrophobic group. In the monolayers, formed in any method of the invention, the amphipathic molecules are aligned on the surface of the hydrophilic body and the hydrated substrate with the hydrophilic groups (or "heads") towards the water interface and the hydrophobic groups (or "tails") away from the water interface.

The amphipathic molecules used in any method of the invention may be lipid molecules, in particular, surfactant molecules may be used. The lipid molecules may be selected from the group comprising fatty acyls, glycerolipids, glycerophospholipids, sphingolipids, sterol lipids, prenol lipids, saccharolipids, polyketides, phospholipids, glycolipids and cholesterol.

The lipid may include any of the group comprising monoolein; 1,2-dioleoyl-sn-glycero-3-phosphocholine (DOPC); 1,2-diphytanoyl-sn-glycero-3-phosphatidylcholine (DPhPC); palmitoyl oleoyl phosphatidylcholine (POPC); 1-palmitoyl-2-oleoyl-phosphatidylethanolamine (POPE); 1-palmitoyl-2-oleoyl-phosphatidylethanolamine; and 1-palmitoyl-2-oleoylphosphatidylglycerol (POPE/POPG) mixtures; or mixtures thereof.

The amphipathic molecules in the monolayers or bilayers may be of the same or different types. For example, each monolayer of the bilayer may comprise a different type of amphipathic molecule such that the bilayer produced is asymmetric. An asymmetric bilayer may be produced using the method of the first aspect of the invention wherein the first monolayer is formed on the hydrated support in a first hydrophobic medium containing a first type of amphipathic molecule. The second monolayer is formed on the hydrophilic body in a second hydrophobic medium containing a second type of amphipathic molecule. The first and second amphipathic molecules may be different. The two monolayers, one on the hydrophilic body and one on the hydrated support, are then brought together in a third hydrophobic medium which does not contain an amphipathic molecule to form an asymmetric bilayer of amphipathic molecules. Alternatively, an asymmetric bilayer may be produced by the second method of the invention by using a different type of amphipathic molecule in the hydrated support to that used in the hydrophilic body.

Alternatively, each monolayer may comprise the same type or mixtures of types of amphipathic molecules.

The hydrated support may comprise a solid or a semi-solid substrate. The terms "solid" and "semi-solid" as used herein are understood to have their ordinary meaning to a person skilled in the art. Essentially the term "solid" refers to a substrate that is rigid and resistant to deformation, and "semi-solid" refers to a substrate that has properties between those of a solid and a liquid. Preferably a semi-solid substrate has some degree of flexibility but is rigid enough to maintain its shape when placed in a container, and will not immediately conform to the shape of the container. An example of a semi-solid substrate is a gel.

Preferably the hydrated support is hydrophilic. Preferably a monolayer of amphipathic molecules will self assemble on the surface of the hydrated support if it is placed in the presence of amphipathic molecules in a hydrophobic medium.

Alternatively, the hydrated support may not be hydrophilic and the lipid monolayer may be formed by the attachment of lipid molecules to the surface, for example, the surface of the support may be such that modified lipids will react with the surface and attach to form a monolayer.

The hydrated support may be porous or non-porous. Preferably the hydrated support is porous.

The hydrated support may be a hydrogel. The hydrogel may be photocrosslinked.

The hydrated support may comprise agarose, polyacrylamide, [cross-linked] polyethylene glycol, nitro-cellulose, polycarbonate, anodisc material, polyethersulphone, cellulose acetate, nylon, Naphion materials, mesoporous silica, water and/or glass.

The hydrated support may be a protein or analyte separation gel, for example, an electrophoresis gel. The separation gel may contain proteins, DNA or other samples separated, for example, on the basis of their size, molecular weight or ionic properties.

The surface of the hydrated support which carries the amphipathic molecule monolayer may be any suitable configuration. The surface may be substantially flat, or the surface may be substantially uneven. The surface may be curved. The surface may be patterned.

The hydrated support may be partially or substantially transparent. Alternatively, the hydrated support may be largely opaque.

The hydrated support may comprise a substrate of any thickness, preferably from about 1 nm to about 10 cm, more preferably from about 1 μm to about 1 cm, most preferably from about 100 μm to about 1 cm.

The hydrophilic body may be a liquid, solid, or semi-solid or a mixture thereof. Preferably the hydrophilic body comprises a droplet of aqueous solution, such as water.

Where the hydrophilic body is a droplet of an aqueous solution it preferably has a diameter of from about 5 nm to 10 cm or more, preferably from 1 μm to 1 mm. In one embodiment, droplets are around 100 μm in diameter.

The hydrophilic body may comprise a hydrated solid or semi-solid support/substrate. The hydrophilic body may comprise a hydrogel, such as hydrated agarose.

The composition of the hydrophilic body is preferably controlled to contain the correct salts to allow an electrical current to be carried, for example, NaCl, KCl, $MgCl_2$ and/or other salts may be included.

The hydrophilic body may also comprise common buffering agents to control pH, for example, Bis-tris, Tris, Hepes, sodium phosphate and/or potassium phosphate.

Salts may also be included for other reasons, for example, to stabilise proteins, to control binding components, to control the osmotic gradient across the bilayer and/or to activate fluorescent probes.

The hydrophilic body may also contain varying amounts of other components, such as, sucrose or PEG which may be used to stabilise osmotic stresses, fluorescent probes, microspheres or beads. The hydrophilic bodies may also comprise denaturants such as urea or guanidine HCl.

Where more than one hydrophilic body is used each may be of the same or a different composition.

The hydrophobic medium may be an oil. The oil may be a hydrocarbon, which may be branched or unbranched, and may be substituted or unsubstituted. For example, the hydrocarbon may have from 5 to 20 carbon atoms, more preferably from 10 to 17 carbon atoms. Suitable oils include alkanes or alkenes, such as hexadecane, decane, pentane or squalene, or fluorinated oils, or silicone based oils, or carbon tetrachloride.

Preferably, the method of the invention uses a lipid (amphipathic molecules) in oil (hydrophobic medium) solution. Preferably the lipid in oil solution contains from about 1 mg/ml to about 30 mg/ml of lipid in the oil. Preferably, the lipid in oil solution contains about 5 mg/ml of lipid. Preferably the lipid/oil solution comprises 1,2-diphytanoyl-sn-glycero-3-phophocholine (DPhPC) in n-hexadecane ($C_{16}$).

The terms "contacting" or "contact" used herein with reference to the contacting of monolayers to form a bilayer are understood to mean actual physical contact, and/or close enough proximity, to allow the assembly of an amphipathic molecule bilayer from separate amphipathic molecule monolayers. Preferably the contacting process is a form of Gibbs-plateau border action.

The bilayer of amphipathic molecules may be from less than about 1 μm to greater than about 1 cm in diameter, preferably from about 5 μm to about 5000 μm in diameter, more preferably from about 30 μm to about 3000 μm in diameter. The bilayer may be from about 5 μm to about 500 μm in diameter, more preferably from about 30 μm to about 300 μm in diameter. The skilled man will appreciate that the bilayer does not need to be circular. Where a non-circular bilayer is formed preferably the bilayer includes a portion which has the aforementioned preferred diameter. For example, a non-circular bilayer according to the invention may include a portion which has diameter from about 1 μm to about 1 cm or more. Preferably, a non-circular bilayer according to the invention has one dimension which is from about 1 μm to about 1 cm or more.

The area of the bilayer of amphipathic molecules may be adjustable. Preferably the area of the bilayer layer is adjustable before, during, or in intervals between uses of the bilayer. The area of the bilayer may be adjustable by increasing or decreasing the contact area between the hydrophilic body and the hydrated support. The contact area between the hydrophilic body and the hydrated support may be adjusted by moving the centre of the hydrophilic body towards or away from the hydrated support, or by moving the hydrated support towards or away from the centre of the hydrophilic body. Preferably to increase the area of the bilayer, the centre of the hydrophilic body is moved towards the hydrated support. Preferably to decrease the area of the bilayer, the centre of the hydrophilic body is moved away from the hydrated support. Where an electrode is used to hold the hydrophilic body, the area of the bilayer may be increased or decreased by moving the electrode towards or away from the hydrated support respectively. In an alternative embodiment the position of the hydrophilic body may be controlled by using an applied electric or magnetic field, by using light beams (such as optical traps) or pressure. The area of the bilayer may be adjusted by increasing or decreasing the volume, size and/or shape of the hydrophilic body. Preferably the area of the bilayer can be changed without breaking the bilayer.

Preferably the area of the bilayer can be moved to any diameter between 5 μm and about 500 μm, or an up to 100 fold change in bilayer size can be achieved, in less than about 10 seconds, less than about 5 seconds, less than about 3 second, less than about 2 seconds, less than about 1 second or less than about 0.5 seconds.

Controlling the area of the bilayer is surprisingly easy and fast. Controlling the area of the bilayer has the advantage of being able to control the number/amount of membrane proteins that associate with the bilayer. Surprisingly, altering the area of the bilayer does not denature or remove membrane-associated proteins from the bilayer. Indeed, if trans-membrane proteins are already inserted into the bilayer they will become concentrated if the area of the bilayer is decreased. If contact between the hydrophilic body and the hydrated support is removed, the bilayer will disassemble and any trans-membrane protein located therein will be no longer present in the bilayer or either monolayer.

The method may include a stabilisation period to allow the monolayer and/or bilayer of amphipathic molecules to form. The stabilisation period may be to allow the system to reach equilibrium. The stabilisation period may be from about 0 seconds to about 5 hours, preferably the stabilisation period is from about 10 seconds to about 1 hour. Preferably the stabilisation period is about 15 minutes. In some embodiments if one component of the method, for example either the first or second monolayer, has been left to stabilise after formation, then there may be no need to allow the other monolayer to stabilise before formation of the bilayer.

The stabilisation period has the advantage of reducing the chances of the hydrophilic body and the hydrated support coalescing without bilayer formation.

The bilayer may be visualised through the hydrated support with an inverted microscope or in some circumstances even by the naked eye. The visualisation of the lipid bilayer may be used to track the formation, position, size, or other property of the bilayer. Visualisation of the bilayer allows labelled analytes/proteins/compounds at or in the bilayer to be seen and studied.

The bilayer of amphipathic molecules may be used to study processes occurring at, in or through the bilayer. The bilayer can be used as an artificial/model system in which to study cell membrane behaviour.

Proteins may be inserted into the bilayer of amphipathic molecules. Proteins in the environment of the bilayer, for example in the hydrophobic medium and/or in the hydrophilic body and/or in the hydrated support, may insert spontaneously into the bilayer. Alternatively proteins may be driven into the bilayer by the application of a voltage and/or by fusion of protein loaded vesicles with the bilayer. The vesicles may be contained within or introduced to the hydrophilic body. Proteins may be introduced into the membrane by using the probe method disclosed in GB0614835.7. Proteins may insert into the bilayer in the same manner as if the bilayer was formed by known techniques.

The inserted protein may be a known membrane-associated protein.

The protein may be a membrane-associated protein which is anchored directly or indirectly to the bilayer. The protein may be a selective or non-selective membrane transport protein, an ion channel, a pore forming protein or a membrane-resident receptor.

Membrane-associated proteins which may associate with and/or insert into the bilayer include any of the group comprising peptides, e.g. gramicidin; α-helix bundles, e.g. bacteriorhodopsin or $K^+$ channels; and β-barrels, e.g. α-hemolysin, leukocidin or *E. coli* porins; or combinations thereof.

The bilayer of amphipathic molecules may be used to detect compounds/analytes which are capable of interaction with amphipathic molecules in the bilayer or with a membrane-associated protein in the bilayer. The interaction with the membrane-associated protein or the amphipathic molecules may be by the specific or non-specific translocation of the analytes/compounds across the bilayer, this may be mediated by the membrane-associated protein or by the amphipathic molecules. Alternatively compounds/analytes may interact with a trans-membrane protein or with the lipid bilayer to cause physical, optical, electrical, or biochemical changes.

Such interaction may be detected in many different ways, including, but limited to, by visual changes, changes in specific capacitance, or by the activation of fluorescently labelled lipids or proteins in the bilayer.

The bilayer may be used to detect membrane-associated proteins. Preferably the membrane-associated proteins are ion channel proteins and/or pore forming proteins. Preferably the membrane-associated proteins diffuse into and/or associate with the bilayer causing a detectable change in the properties at the bilayer. The properties changed may be physical, optical, electrical or biochemical.

Bilayers of amphipathic molecules made by any method of the invention may be used to investigate and/or screen membrane-associated proteins; to investigate and/or screen for analytes that interact with membrane-associated proteins; and to investigate and/or screen for compounds that interact with bilayers made of different amphipathic molecules. Bilayers of different amphipathic molecules may be screened to study the role of and/or the interaction of different amphipathic molecules with various analytes/compounds.

The bilayer may be used to study the voltage dependence properties of a membrane-associated protein inserted in the bilayer. For example, a bilayer composed of DPhPC may have a specific capacitance between about 0.3 and about 0.9 μF $cm^{-2}$ at 22° C., preferably about 0.65 μF $cm^{-2}$ at 22° C. By studying changes in the specific capacitance properties the changes in the properties of the bilayer caused by different conditions can be studied. For example, by studying the ionic current crossing a bilayer the properties of an ion permeable transmembrane-associated protein may be studied, as may the interaction of the transmembrane-associated protein with different analytes/compounds.

The bilayer may be used to study the ability of a membrane-associated protein inserted in the bilayer to transport molecules across the membrane. For example, the amount of a molecule being transported across a membrane, either through a protein or simply non-mediated transport across the bilayer, may be determined by using voltage studies, mass spectrometry, enzymatic techniques, such as ELISA, or by using a fluorescently or radioactively labelled substrate.

A bilayer produced by any method of the invention may also be used to study the effects of mechanical changes of the bilayer on proteins in the bilayer or on the bilayer itself. Mechanical changes which can be studied include, for example, changes in membrane curvature, lateral forces, surface tension etc.

A compound/analyte to be tested, studied and/or used in a screen may be introduced into the system by placing it in the hydrophilic body and/or in the hydrated support and/or in the hydrophobic medium. If included in the hydrophilic body the compound/analyte may be incorporated when the body is formed or it may be added later, for example, by injection into the formed body. Similarly, if the compound/analyte is in the hydrated support it may be incorporated when the support is formed or added later.

In one embodiment the hydrated support may be a protein separation gel or membrane containing proteins (analytes/compounds) for analysis. For example the sample may be a polyacrylamide gel containing proteins which have been separated on the basis of size. In this embodiment the analytes/compounds are introduced to the bilayer via the hydrated support.

The analyte/compound may be a purified protein or a crude protein extract.

The analytes/compounds to be tested may be in a sample. The sample may be an environmental sample, for example from a body of water such as a river or reservoir, or the sample may be a biological sample, for example a sample of blood, urine, serum, saliva, cells or tissue. The sample may be a liquid from a cell growth medium.

One or more detection means may be used to detect chemical, biochemical, electrical, optical, physical and/or environmental properties of the bilayer of amphipathic molecules or of membrane-associated proteins inserted into the bilayer. In particular the one or more detection means may be used to detect changes in or at the bilayer induced by the compounds/analytes.

The detection means may comprise electrodes which may be used to detect changes in ionic current passing through a protein channel inserted into a bilayer or the electrochemical properties of molecules in the hydrated support, hydrophilic body or bilayer.

Chemical or biochemical changes may be detected using enzymatic assays or immunoassays. Alternatively, the use of labelled, for example radio or fluorescently labelled, proteins which are activated under certain conditions can be used to monitor changes at the bilayer. Colormetric methods that respond to changes in light absorption upon reaction may also be used to detect changes in the bilayer, in particular this method may be used to detect a change in the size of the bilayer.

The detection means may be capable of constantly or intermittently detecting properties of, or changes at, the bilayer.

Detection reagents, like membrane-associated proteins, analytes and other compounds may be delivered to the bilayer by incorporation into the hydrophilic body and/or the hydrated support, injection directly into the hydrophilic body and/or the hydrated support, and/or incorporation in, or addition to, the hydrophobic medium. Injection into the hydrophilic body and/or the hydrated support may be achieved using a micropipette.

In an embodiment where changes in membrane capacitance are being studied electrodes may be used as the detection means. The electrodes may be Ag/AgCl, such electrodes may be from approximately 10 microns to 1 mm in diameter. A first electrode may be electrically contacted with the hydrophilic body and a second electrode may be electrically contacted with the hydrated support. Electrical properties of the bilayer, such as the specific capacitance of the bilayer, may be determined using the electrodes.

A micromanipulator may be used to insert electrodes into the hydrophilic body and/or the hydrated support.

The physical, chemical or electrical environment of the bilayer may be controlled by the introduction, removal, or sequestering of reagents, analytes, compounds and/or proteins to or from the bilayer and/or hydrophilic body and/or hydrated support, e.g. the pH of the environment surrounding the bilayer may be controlled by the addition of a buffer to the hydrophilic aqueous body and/or the hydrated support.

The bilayer may be repeatedly reformed, by removing contact between the hydrophilic body and the hydrated support and then re-establishing contact to re-form the bilayer. The bilayer may be disassembled by increasing the distance between the centre of the hydrophilic body and the hydrated support to a point where the bilayer would become unstable and spontaneously disassemble.

Membrane-associated proteins in the bilayer may be removed from association with the bilayer by disassembling the bilayer for example by removing contact between the hydrophilic body and the hydrated support. Once the bilayer has been disassembled to remove the membrane-associated proteins, it may be reformed such that no membrane-associated proteins, or different membrane-associated proteins, are associated with the bilayer.

The concentration of membrane-associated proteins associated with the bilayer may be increased by decreasing the area of the bilayer. Conversely, the concentration of membrane-associated proteins associated with the bilayer may be decreased by increasing the area of the bilayer.

The ability to increase the concentration of membrane-associated proteins in the bilayer may be used to produce 2D crystals of membrane-associated proteins by decreasing the area of the bilayer comprising the membrane-associated proteins and hence restricting the area within which a membrane protein can diffuse.

The ability to increase or decrease the concentration of membrane-associated proteins in the bilayer may be used to modulate protein-protein interactions, for example between sub-units of a protein or between components of a protein complex.

Once formed, a bilayer made according to any method of the invention may be translocated or moved across the surface of the hydrated support. Preferably this is achieved by moving the hydrophilic body across the surface of the hydrated support. The lipid bilayer may be translocated across the surface of the hydrated support at speeds of about 1 or 2 mm $s^{-1}$ or more. Preferably membrane-associated proteins within the bilayer do not disassociate from the bilayer when the bilayer is translocated across the surface of the hydrated support.

The translocation of the bilayer across the surface of the hydrated support may be achieved by moving a member contacted with the hydrophilic body or the hydrated support. Preferably the member is an electrode. Preferably a micromanipulator is used to move the member in order to translocate the bilayer by moving either the hydrophilic body across the hydrated support or the hydrated support across the hydrophilic body. Alternatively both the hydrated support and the hydrophilic body may move.

The translocation of the bilayer may be used to apply forces to proteins in the bilayer, for example to study mechano-sensitive protein channels or to study the effect of such force on the properties of the bilayer itself.

The translocation of the bilayer may be used to scan across the surface of the hydrated support to identify analytes/compounds in the hydrated support which alter properties of the bilayer and/or membrane-associated proteins in the bilayer.

The surprising capability of the bilayer to translocate across the surface of the hydrated support provides the benefit of being able to scan across the hydrated support with the bilayer to detect analytes/compounds, such as membrane-associated proteins and/or reagents or substrates located at different regions of the same hydrated support. This advantageously can be done without having to disassemble the bilayer between each sampling region.

The bilayer may be translocated across a hydrated support comprising an array or library of different compounds. The different compounds may be spotted onto the support in predetermined positions. Alternatively the hydrated support may comprise a separation gel or membrane, containing compounds such as proteins or DNA, that have been separated on the basis of their size or ionic properties.

The translocation of one or more bilayers may allow a bilayer comprising one or more particular membrane-associated proteins to be rapidly screened against a library of compounds in the hydrated support. The screen may allow compounds in a library which interact with a membrane-associated protein and cause a detectable change in properties at the bilayer to be detected. The compounds in the library may be proteins, DNA or other small molecules. The detectable change may be, for example, a change in conductance or a change in fluorescence or other marker pattern.

Alternatively, or additionally, translocation of the bilayer may allow a library of compounds in a hydrated support to be screened for potential membrane-associated proteins. Again, the membrane-associated proteins may be detected by a change in properties at the bilayer, for example, a change in conductance or capacitance across the membrane. The library may comprise protein extracted from a cell or a population of cells.

The bilayer may be formed on a porous hydrated support which may then be scanned across the surface of a cell to detect local concentration differences in excreted compounds, such as ATP. The cell may be prokaryotic or eukaryotic. The bilayer may be used to detect analytes/compounds, such as cell excretions, on a cell surface in vitro or in vivo.

The bilayer may be formed on a suspended hydrated support in a mobile device, such as a pipette tip, which may then be scanned across the surface of a cell. Alternatively the mobile device may be used to probe different solutions, for example, different biological samples.

A plurality of separate bilayers may be formed between a plurality of separate hydrophilic bodies and one or more hydrated supports. A hydrophilic body may be contacted with one or more other hydrophilic bodies on the same hydrated support to form a plurality of separate lipid bilayers between each of the hydrophilic bodies as well as between the hydrophilic bodies and the hydrated support. The hydrophilic bodies may be arranged in a two, or potentially three, dimensional array.

Two or more separate hydrophilic bodies on the same hydrated support may comprise the same or different detection means and/or different reagents, and/or the same or different membrane-associated proteins relative to each other.

An array of aqueous droplets may be deposited over a hydrated support surface to detect the location of analytes/compounds in the hydrated support, for example by the fluorescence of a hydrophilic body or a change in recorded conductance when an analyte/compound is detected.

According to another aspect the invention provides a bilayer product comprising a hydrophilic body and a hydrated support with a bilayer of amphipathic molecules therebetween. Preferably the bilayer is formed by interaction of a monolayer of amphipathic molecules on the hydrophilic body and a monolayer of amphipathic molecules on the hydrated support.

The bilayer may be formed by any method of the invention.

The skilled man will appreciate that all the preferred features discussed with reference to the first or second aspect of the invention, and in particular those relating to the bilayer itself and not its production, can be applied to a bilayer product according to the invention and to all aspects of the invention which use a bilayer.

According to another aspect of the invention, there is provided the use of a bilayer product according to the invention in conjunction with fluorescence microscopy.

The nature of the hydrated support preferably allows the bilayer to be viewed using a microscope. Thus in this aspect of the invention the hydrated support preferably is a layer no more than about 2 mm thick. Preferably the hydrated support is from about 1 nm to about 2 mm thick, preferably from about 100 nm to about 1 mm thick, more preferably the hydrated support is from about 100 nm to about 400 nm thick.

Preferably when a thin hydrated support of less than about 400 nm thick is used it is kept in contact with a re-hydrating medium, such as a larger bulk of hydrating liquid or hydrated support material, to prevent drying out of the thin support material. The rehydrating medium may be the same or different in material/composition to the thin hydrated support, and is present to prevent the thin layer from dehydrating. The rehydrating support may be agarose gel, water or polyacrylamide gel. The rehydrating support may be porous or solid.

Molecules to be observed may be fluorescently labelled with fluorophores.

Preferably fluorophores in the hydrophilic droplet and/or hydrated support are observed using total internal reflection fluorescence. Preferably observations using total internal reflection fluorescence are used in combination with electrical measurements.

Total internal reflection fluorescence microscopy may be used to observe fluorescence from entities present in the bilayer either as a bulk property of the bilayer, or with suitable detection down to the level of individual molecules.

The advantage of using total internal reflection fluorescence to observe the fluorophores is that only fluorophores within about 200 nm of the lipid bilayer are illuminated and thus observed, whilst other fluorophores not close to the lipid bilayer are not illuminated and not observed. Using total internal reflection fluorescence measurements in combination with electrical measurements has the advantage that protein-protein interactions can be studied, for example, the assembly of channel proteins such as $\alpha$-hemolysin from labelled subunits or the electrical response of ion channels to the binding of a fluorescent substrate can be studied.

According to a yet further aspect of the invention there is provided a method of screening for an interaction between a bilayer of amphipathic molecules and one or more compounds in a library comprising:
  i) providing a bilayer product comprising a hydrophilic body and a hydrated support with a bilayer of amphipathic molecules therebetween;
  ii) translocating the hydrophilic body and thus the bilayer across the surface of the hydrated support; and
  iii) detecting any interaction between the bilayer and a compound in the hydrated support.

Preferably the bilayer product is made by the method of the first or second aspect of the invention.

Preferably the hydrated support comprises the library of compounds to be tested.

In one embodiment a membrane-associated protein may be inserted into the bilayer before or as the bilayer is translocated across the hydrated support.

Translocation of the bilayer may be achieved by the direct or indirect contact of the hydrophilic body with a micromanipulator arranged to move the hydrophilic body. The hydrophilic body may be in contact with an electrode which may be moved to translocate the bilayer across the hydrated support.

The method of screening may be automated to allow high throughput screening to be undertaken.

The skilled man will appreciate that the preferred features of any aspect of the invention relating the method of producing a bilayer, to a bilayer per se and to the translocation of a bilayer can be applied to this aspect of the invention.

According to a further aspect of the invention, there is provided the use a bilayer product according to the invention to identify one or more membrane-associated protein present in and/or on the hydrated support or the hydrophilic body.

According to another aspect of the invention, there is provided the use of a bilayer product according to the invention to identify substances capable of interaction with a membrane-associated protein located in the bilayer.

According to another aspect of the invention, there is provided a method for detecting one or more analytes present in an aqueous solution comprising the steps of:
  (a) providing a lipid-in-oil solution in a walled vessel, wherein at least part of a wall of the vessel comprises a porous hydrated support;
  (b) providing a hydrophilic body in the lipid-in-oil solution;

(c) forming a first monolayer of lipid molecules on the surface of the porous hydrated support and a second monolayer of lipid molecules on the surface of the hydrophilic body;

(d) contacting the porous hydrated support with the hydrophilic body such that a lipid bilayer forms between the lipid monolayer on the hydrophilic body and the lipid monolayer on the porous hydrated support;

(e) contacting the porous hydrated support with the aqueous solution such that the analytes present in the aqueous solution are available to the lipid bilayer;

(f) detecting the insertion of analytes into the lipid bilayer and/or the translocation of the analytes across the lipid membrane and/or the interaction of analytes with the bilayer, using detection means.

An apparatus for use with a lipid bilayer comprising a walled vessel for retaining a lipid/oil solution, wherein at least one portion of a wall of the vessel comprises a porous support arranged to be hydrated in use.

The apparatus may comprise a detection means. Preferably the detection means is an electrode or a photodetector.

Preferably the apparatus is portable. Preferably the apparatus is handheld.

The walled vessel may be a pipette tip.

It will be appreciated that all the optional and/or preferred features of the invention discussed in relation to only some aspects of the invention can be applied to all aspects of the invention.

BRIEF DESCRIPTION OF THE DRAWINGS

Preferred embodiments/aspects of the invention will now be described by way of example only with reference to the accompanying figures, in which:

FIG. 1A is a diagram of a droplet-on-hydrated-support bilayer. A lipid monolayer spontaneously forms on the aqueous surface of the aqueous (water) droplet and the hydrated support (hydrogel) when each is immersed in a solution of lipid in hydrophobic oil. When the monolayers of the two components are brought into contact they form a lipid bilayer; FIG. 1B shows a droplet bilayer (DHB) visualised from below with an inverted microscope—the image shows a droplet, without an electrode, supported on a hydrogel surface. The single continuous bilayer area in the centre of the droplet is easily seen due to the large change in refractive index at the interface; FIG. 1C demonstrates that the lipid bilayer between the droplet and hydrated support can be electrically accessed via electrodes inserted into both the droplet and the hydrated support. The electrical capacitance trace shows the formation of a lipid bilayer. Bilayer capacitance is determined by applying a triangular potential waveform to the lipid bilayer and measuring the square wave peak-to-peak current response;

FIGS. 2A and B show composite images of polyacrylamide gels after droplet-on-hydrated-support bilayer scanning, created by overlaying an image of the dried gel (containing visible pre-stained maker lane M) with autoradiographs to visualise the radio-labelled protein bands. Marker lane (M) bands correspond to molecular weights of approximately 210, 111, and 71 kDa; FIG. 2A is an SDS-PAGE gel containing the potassium channel Kcv; FIG. 2B is an SDS-PAGE gel containing the pore forming protein alpha hemolysin (αHL) αHL-WT (WT) and αHLM113F-D8 (113F) which forms heptameric protein pores. After immersion in DPhPC/C16 (lipid/oil) solution the gels were scanned with 200 nL aqueous droplets which had formed a bilayer on contact with the gel (hydrated support). Protein insertion and binding at the bilayer was monitored via patch-clamp amplified electrical recordings as a function of droplet-bilayer position on the gel surfaces; FIG. 2C shows typical electrical recordings from the regions of the gels containing Kcv (+20 mV, 500 mM KCl, 10 mM Hepes, pH 7.0), αHL-WT and αHL-M113F-D8 (+10 mV, 1 M KCl, 10 mM $Na_iPO_4$, pH 7.0). The αHL channels were scanned with droplets containing 10 μM β-cyclodextrin (βCD) to differentiate between the two mutants; FIG. 2D shows that channel-protein insertion was only observed in localised regions about the separated protein bands. This is illustrated by a 12 mm linear scan across the αHL-WT band (dotted line marked on gel in FIG. 2B), which shows the rate of channel-protein insertion as a function of bilayer position;

FIG. 3A shows a coomassie stained polyacrylamide gel after droplet-on-hydrated-support bilayer scanning, showing SDS-PAGE purified *E. coli* cell extracts. The *E. coli* cell lines were separately transformed to produce αHL-WT (lane 1) and αHL-M113F-D8 (lane 2) through leaky expression. After immersion in $DPhPC/C_{16}$ solution the gel was scanned with 200 nL droplets containing 10 μM β-cyclodextrin. Protein insertion and binding in the bilayer was monitored via patch clamp amplified electrical recordings as a function of droplet-bilayer position on the gel surface; FIG. 3B shows typical electrical recordings from scans of the regions circled on the gel. Large numbers of αHL-WT (top) and αHL-M113F-D8 (middle) channels inserted from the regions indicated. Small numbers of unidentified porin-like channels (bottom) were found in the lower region of the gel;

FIG. 4A shows a schematic of the experimental approach employed to scan molecules doped into polyacrylamide gels by absorption. γ-cyclodextrin (γCD) and heptakis(2,3,6-tri-O-methyl)-β-cyclodextrin (hβCD) were introduced to the bottom of the gel approximately 10 mm apart. After immersion and stabilisation in the lipid/oil solution the gel was scanned with droplets containing αHL-WT channels. Cyclodextrin binding to αHL-WT channels in the droplet bilayer was monitored via patch clamp amplified electrical recordings as a function of droplet-bilayer position on the gel surface; FIG. 4B shows the binding characteristics of γCD (top, 68% block) and hβCD (bottom, 95% block) to αHL-WT are clearly distinguishable in electrical recordings (−50 mV, 1 M KCl, 10 mM $Na_iPO_4$, pH 7.0); FIG. 4C shows the binding frequency of the two cyclodextrins plotted as a function of distance in a scan between the two doped locations. Lines indicate Gaussian fits to the measured binding frequency;

FIG. 11A—shows independent/separate droplets; FIG. 11B—shows connected droplets forming multiple lipid bilayers between the droplets and with the underlying hydrated support;

EXAMPLES

Figure 1:
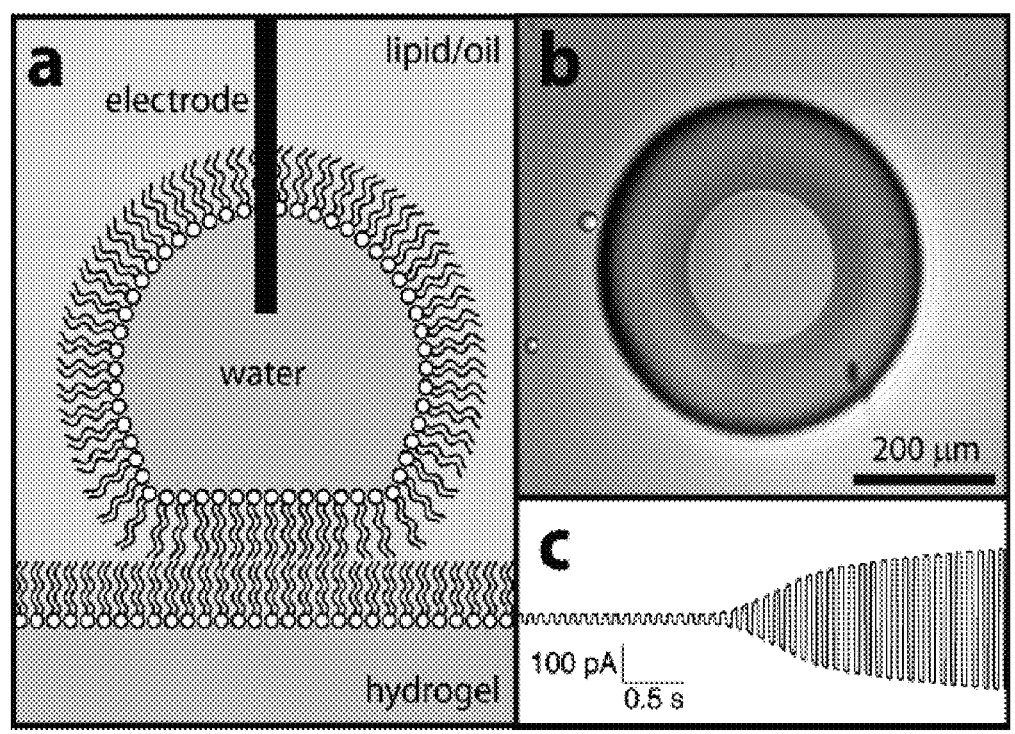
FIG. 1—illustrates an aqueous droplet (hydrophilic body) on a hydrated support bilayer, referred to herein in as a droplet-on-hydrated-support bilayer (DHB)

"A droplet-on-hydrated-support bilayer" as referred to in the specific examples is the same as "a bilayer of amphipathic molecules" as previously discussed.

Methods 1,2-Diphytanoyl-sn-glycero-3-phosphocholine (Avanti Polar Lipids), hexadecane (Sigma-Aldrich), β-cyclodextrin (Sigma-Aldrich), and γ-cyclodextrin (Sigma-Aldrich), heptakis(2,3,6-tri-o-methyl)-β-cyclodextrin (Cyclolab) were used without further purification.

In vitro Transcription/Translation of Proteins

αHL-WT, αHL-M113F-D8 (Gu, L. Q. et al., 2001. *Journal of General Physiology* 118, 481-493) (RL2 background (Cheley, S. et al., 1999. *Protein Science* 8, 1257-1267) and a C-terminal D8 extension to produce a gel shift relative to αH-WT) and Kcv were prepared from genes cloned in the pT7.SC1 vector (Cheley, S. et al., 1997. *Protein Engineering* 10, 1433-1443) using a coupled in vitro transcription/translation (IVTT) kit (Promega Corporation) as previously described (Walker, B. et al., 1992. *Journal of Biological Chemistry* 267, 10902-10909). $^{35}$S-methionine was incorporated into the proteins for visualisation by autoradiography.

50 μL in vitro transcription/translation reactions of αHL proteins were oligomerised as described previously (Walker, B. et al., 1992. *Journal of Biological Chemistry* 267, 10902-10909), then pelleted and resuspended (20 μL, 10 mM MOPS buffer, pH 7.4, 150 mM NaCl, 1 mg mL$^{-1}$ BSA). Prior to electrophoresis, the 20 μL resuspended oligomer samples were mixed with 5 μL of 5×SDS-containing Laemmli buffer (final concentration: 10% (v:v) glycerol, 5% 2-mercaptoethanol, 2.3% SDS, 0.0625 M Tris, pH 7.5).

100 μL in vitro transcription/translation reactions were performed for Kcv, and the products were subsequently separated in a 10% Tris-HCl gel by electrophoresis. The gel was dried onto paper under vacuum at room temperature and then imaged by autoradiography. The band corresponding to the Kcv tetramer was cut from the gel and rehydrated (300 μl, 10 mM Hepes, pH 7.4). The rehydrated gel was crushed and transferred to a 0.2 μm cellulose acetate microfiltration tube (Rainin) and centrifuged at 25000 g for 30 minutes to recover the solubilised protein.

Electrophoresis of In vitro Transcription/Translation Proteins

5 μL aliquots of the gel-purified Kcv tetramers were loaded into 8.5% Tris-acetate polyacrylamide gels and subjected to electrophoresis (200 V, 20 minutes) in TBE buffer (8.9 mM Tris, pH 8.3, 8.9 mM boric acid, 200 μM EDTA, 0.1% SDS) to separate the protein bands. The gel tank was then refilled with SDS-free TBE buffer, and electrophoresis was continued (50 V, 2 hours) to remove SDS in the gel.

5 μL aliquots of the in vitro transcription/translation α-hemolysin oligomers were loaded into 7% Tris-acetate polyacrylamide gels (XT Criterion; Bio-Rad Laboratories Inc.) and subjected to electrophoresis (200 V, 1 hour) in XT Tricine buffer (Bio-Rad Laboratories Inc.) to separate the protein bands. The gel tank was then refilled with SDS-free Laemmli buffer, and electrophoresis was continued (100 V, 2 hours) to remove SDS.

All gels were run with a pre-stained marker lane (SeeBlue Plus2, Invitrogen). Following droplet-on-hydrated-support bilayer gel scanning the gels were imaged by autoradiography.

*E. Coli* Crude Extraction and Electrophoresis

Competent *E. coli* JM109(DE3) cells (Promega Corporation) were transformed by heat-shock with pT7-plasmids encoding either αHL-WT or αHL-M113F-D8. Single colony transformants were picked and cultured for 16 hours in 2 mL LB-medium containing 50 μg mL-1 ampicillin. The cells were then centrifuged at 2500 g for 20 minutes and resuspended (200 μL, 25 mM MOPS, pH 7.4, 150 mM NaCl, 0.5% (w:v) SDS, 500 ng DNase 1). Following 30 minutes of incubation on ice the 200 μL samples were mixed with 50 μL of 5×SDS-containing Laemmli buffer (final concentration: 10% (v:v) glycerol, 5% 2-mercaptoethanol, 2.3% SDS, 0.0625 M Tris, pH 7.5). 45 μL of this solution was then loaded into 10% Bis-Tris polyacrylamide gels (XT Criterion; Bio-Rad Laboratories Inc.) and subjected to electrophoresis (200 V, 30 minutes) in XT MOPS buffer (Bio-Rad Laboratories Inc.). The gel tank was then refilled with SDS-free buffer (50 mM MOPS, 50 mM Bis-Tris, pH 7.0), and electrophoresis was continued (100 V, 2 hours) to remove SDS.

Following droplet-on-hydrated-support bilayer gel scanning the gels were stained with Coomassie Brilliant Blue (Sigma-Aldrich).

Droplet-on-hydrated-Support Bilayer Gel Scanning

After electrophoresis the Kcv gels were immersed in 10 mM Hepes buffer (pH 7.0) containing 500 mM KCl for at least 30 minutes. The αHL and *E. coli* gels were immersed in 10 mM Na$_2$PO$_4$ (pH 7.0) buffer containing 1M KCl. After dialysis the gels were left in 10 mM DPhPC/C$_{16}$ solution for 15 minutes, then scanned with approximately 200 nL droplets of the same buffer as that in the gel. Droplets were moved about the surface of the hydogels with the inserted Ag/AgCl electrode attached to a dxdydz micromanipulator (NMN-21; Narishige).

Electrical Measurements and Bilayer Imaging

100 µm diameter Ag/AgCl wire electrodes were used to electrically access the droplets and gels. Currents were recorded with a patch clamp amplifier (Axopatch 200B; Axon Instruments), and digitized at 1 kHz (MiniDigi-1A; Axon Instruments). Electrical traces were filtered post-acquisition (100 Hz lowpass Gaussian filter) and analyzed using pClamp 9.0 software (Axon Instruments). The gel scanning apparatus and amplifying headstage were enclosed in a Faraday cage attached to an inverted microscope (TE-2000; Nikon Instruments UK) equipped with a camera (DS-1QM; Nikon) for imaging and positional tracking of the droplet-on-hydrated-support bilayers.

Results

Creating Droplet-on-hydrated-Support Bilayers 10 mM 1,2-diphytanoyl-sn-glycero-3-phosphocholine (DPhPC) in hexadecane ($C_{16}$) was used as the lipid/oil solution in all experiments. Aqueous volumes immersed in this solution spontaneously self-assemble a DPhPC monolayer, and when the monolayers of two components are brought into contact they spontaneously form a lipid bilayer (Tsofina, L. M. et al., 1966. *Nature* 212, 681-683; Malmstadt, N. et al., 2006. *Nano Letters* 6, 1961-1965; Funakoshi, K. et al., 2006. *Analytical Chemistry* 78, 8169-8174; Holden, M. A. et al., 2007. *Journal of the American Chemical Society*—in press). A droplet-on-hydrated-support bilayer is formed by contacting aqueous droplets with porous hydrated supports such as hydrogels (FIG. 1A). A stabilisation period of at least 15 minutes was required before contacting monolayers to prevent fusion. After this period, bilayer formation was observed with almost 100% efficiency within a few seconds to a minute of contact of an aqueous droplet with the hydrated support. The droplet-on-hydrated-support bilayers were visualised on an inverted microscope (FIG. 1B), this technique was used to track the position of a lipid bilayer during experiments.

The lipid bilayers were electrically accessed by inserting a 100 µm diameter Ag/AgCl electrode into the droplets (FIG. 1A) using a micromanipulator. With a corresponding Ag/AgCl ground electrode in the hydrated support, electrical measurements across the lipid bilayer were carried out. The lipid bilayers were typically able to withstand voltages up to approximately 300 mV while retaining seals in excess of 100 GΩ. Electrical noise levels were typically of the order of ±0.5 pA rms with a 1 kHz recording bandwidth. This reflects the limitations of this apparatus and not the inherent noise in droplet-on-hydrated-support bilayers.

Synchronous optical measurements of bilayer area (FIG. 1B) in conjunction with capacitance measurements (FIG. 1C) yielded a specific capacitance of 0.65 µF cm$^{-2}$ at 22° C. for the DPhPC bilayers in this system. This agrees well with other reported values (0.4 to 0.8 µF cm$^{-2}$) (Montal, M. & Mueller, P. 1972. *Proceedings of the National Academy of Sciences of the United States of America* 69, 3561-3566; Fujiwara, H. et al. 2003. *Journal of Chemical Physics* 119, 6768-6775; Funakoshi, K. et al., 2006. *Analytical Chemistry* 78, 8169-8174), indicating the lipid bilayers are similar in thickness to their planar bilayer counterparts.

Gel Scanning with Droplet-on-hydrated-Support Bilayers

By scanning the position of a bilayer across a gel while making single-channel recording measurements it is possible to resolve the location of isolated membrane channels as they insert into the lipid bilayer. When applied to electrophoretically separated protein bands in hydrogels, scanning allows the determination of whether a particular band contained a channel-forming protein. To validate this technique, polyacrylamide gels containing the viral potassium channel Kcv (Plugge, B. et al., 2000. *Science* 287, 1641-1644; Gazzarrini, S. et al., 2003. *Febs Letters* 552, 12-16), and two mutants of the *staphylococcal* pore forming toxin α-hemolysin (αHL) (Song, L. Z. et al., 1996. *Science* 274, 1859-1866) were scanned.

Figure 2:
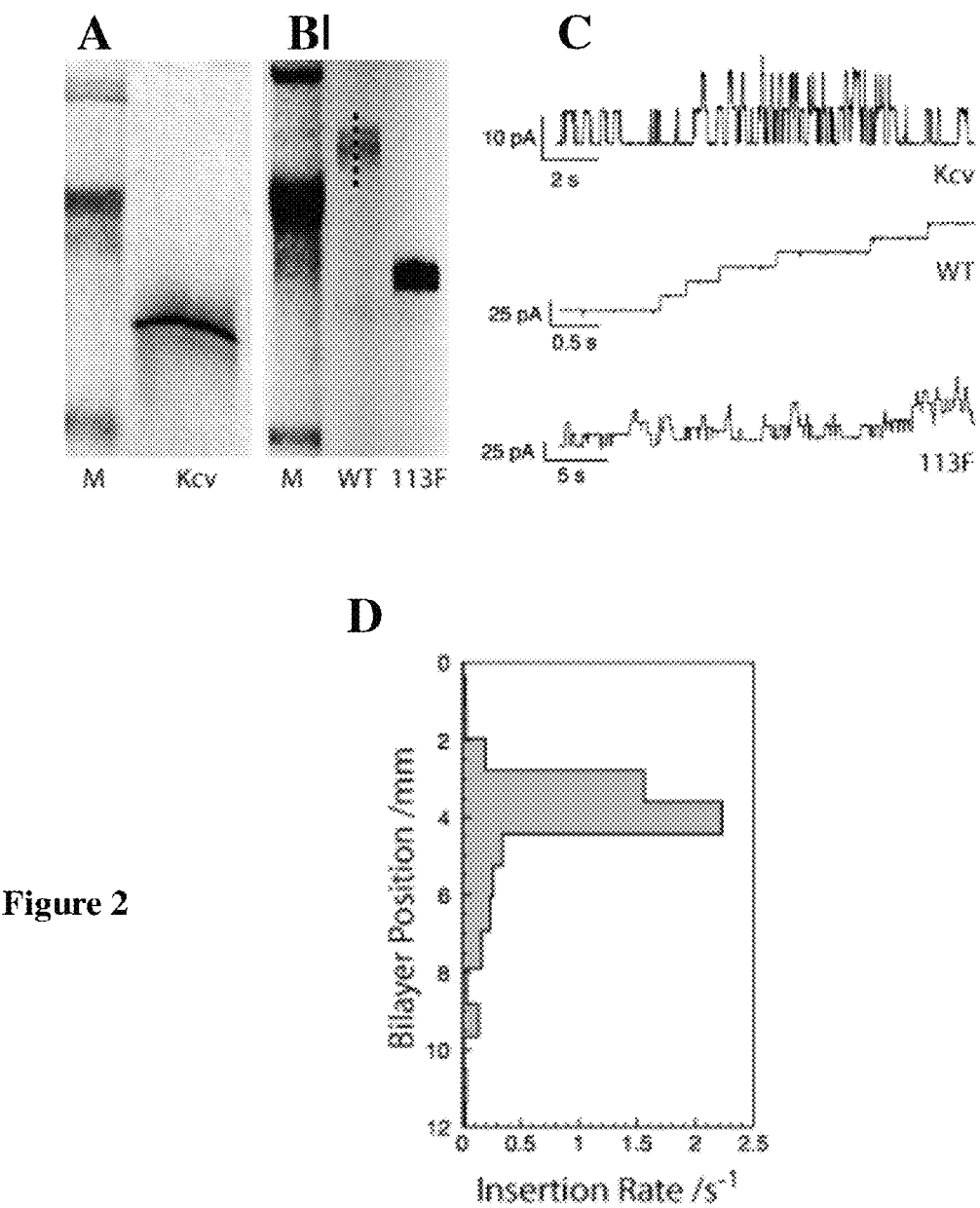
FIG. 2—illustrates the scanning of proteins in hydrogels using a droplet-on-hydrated-support bilayer.

SDS-PAGE was used to separate in vitro transcription/translation (IVTT) expressed Kcv, wild-type α-hemolysin (αHL-WT) and a M113F α-hemolysin mutant (αHL-M113F-D8) (Gu, L. Q. et al., 2001. *Journal of General Physiology* 118, 481-493) in polyacrylamide gels (FIG. 2A and FIG. 2B). SDS-PAGE was followed by electrophoretic cleaning to remove free SDS from the gels (which would otherwise destabilise the lipid bilayer). This step can be omitted when running gels under native detergent-free conditions. After electrophoresis, the gels were dialysed in appropriate buffers containing KCl to introduce the electrolyte necessary for electrical recordings. Following dialysis the gels were immersed in the DPhPC/$C_{16}$ lipid/oil solution for 30 minutes, and then scanned with 200 nL droplets (producing bilayers of approximately 200 µm in diameter). The droplets were moved about the surface of the hydrogels by translating an inserted Ag/AgCl electrode, and the lipid bilayer position was tracked visually on an inverted microscope.

When droplet-on-hydrated-support bilayers were positioned over regions of the gels containing channel proteins stepwise changes in ion-current resulting from the spontaneous insertion of channels could be detected. FIG. 2C shows typical examples of electrical traces acquired when scanning the respective regions of the gels containing Kcv, αHL-WT and αHLM113F-D8. Kcv behaviour is characterised by stepwise bursts of current as the channels transiently open and close (FIG. 2C top). αHL-WT pores remain open, resulting in stepwise increases in current for each insertion event (FIG. 2C middle).

To demonstrate the ability to differentiate between the two α-hemolysin mutants the αHL gels were scanned with droplets containing β-cyclodextrin (βCD). β-cyclodextrin acts as a non-covalent blocker that lodges inside the β-barrel of αHL, which is observed as a reversible stepwise change in current in an electrical recording (Gu, L. Q. et al., 1999. *Nature* 398, 686-690; Gu, L. Q. & Bayley, H. 2000. *Biophysical Journal* 79, 1967-1975). αHL-WT does not bind β-cyclodextrin strongly (Gu, L. Q. et al., 1999. *Nature* 398, 686-690; Gu, L. Q. & Bayley, H. 2000. *Biophysical Journal* 79, 1967-1975), whereas the αHL-M113F-D8 mutant binds β-cyclodextrin strongly with a voltage-dependent mean dwell time of approximately 10 seconds (Gu, L. Q. et al., 2001. *Journal of General Physiology* 118, 481-493). Without β-cyclodextrin the electrical characteristics of the two αHL variants are essentially identical. With β-cyclodextrin the αHL-M113F-D8 channels are easily distinguishable by the β-cyclodextrin binding events overlaying the stepwise increases in conductance (FIG. 2C bottom).

It was found that during gel scanning the proteins did not appear to diffuse, and insertion events were only observed in highly localised regions about the focused bands in the gel. This is illustrated quantitatively in FIG. 2D, which shows protein insertion rate in a linear scan across the wild-type αHL band using a droplet with a lipid bilayer of approximately 200 µm in diameter.

Figure 3:
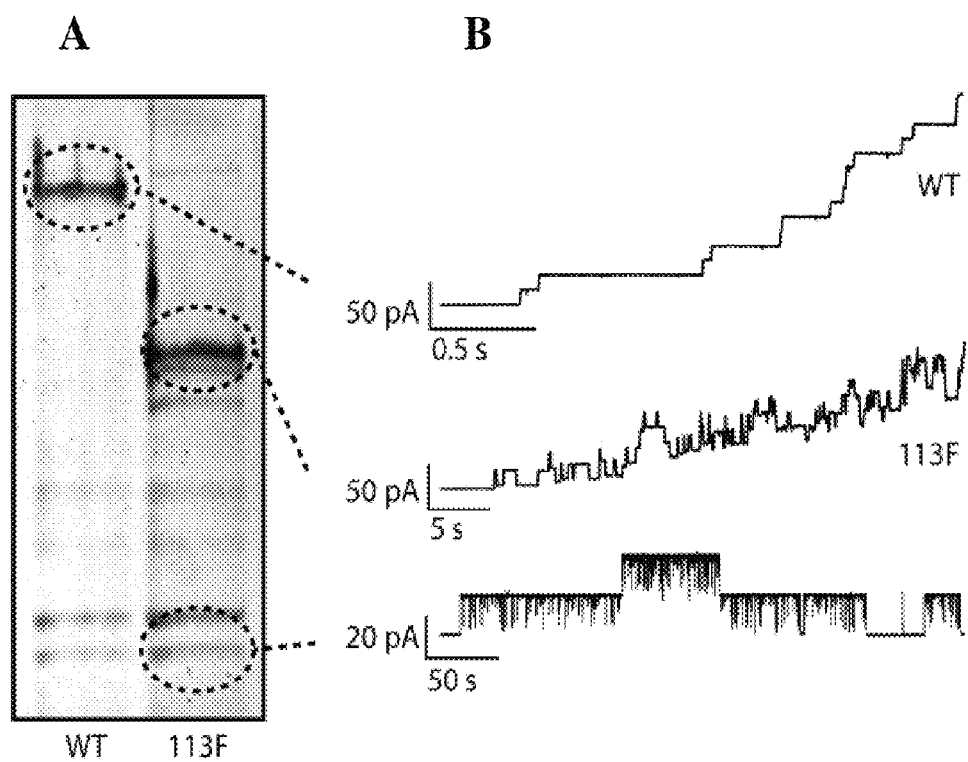
FIG. 3—illustrates the results of scanning cell extracts in gels using droplet-on-hydrated-support bilayers.

The gel scanning experiments where extended to SDS-PAGE purified cell extracts. FIG. 3 shows the results of scanning a SDS-PAGE gel (FIG. 3A) containing crude extracts from *E. coli*, transformed to produce αHL-WT (lane 1) and αHL-M113F-D8 (lane 2) through leaky expression. As with the previous gel example in FIG. 2, these proteins could be electrically characterised (FIG. 3B) from the expected regions of the gel as shown by subsequent Coomassie staining. Channel insertion rates were higher than observed from the in vitro transcription/translation gels, reflecting the substantially higher concentrations of protein produced from expression in *E. coli*. Surprisingly, in addition to αHL channels a number of other channel proteins were detected with markedly different behaviour (e.g. FIG. 3B bottom), again localised to specific areas of the gel. The channels typically insert in multiples of three and show substantial voltage-dependent gating behaviour.

It was found that extended immersion in the lipid/oil solution during gel scanning does not result in any substantial loss of protein from the gel matrix. Similarly, extended immersion in electrolyte buffer during the dialysis step does not noticeably deplete the proteins in the gel. As a result, individual gels can be re-used in many, at least six, consecutive gel scanning experiments, and the gel buffer conditions can be varied as required. Furthermore, the scanning procedure does not affect the ability to subsequently stain or image the gel, or to recover specific proteins from the gel for further analysis.

Analyte Detection with Droplet-on-hydrated-Support Bilayers

Essentially reversing the gel scanning experiment, protein channels in droplets on hydrated support bilayers can be used as molecular sensors to scan different analytes within hydrogels.

Figure 4:
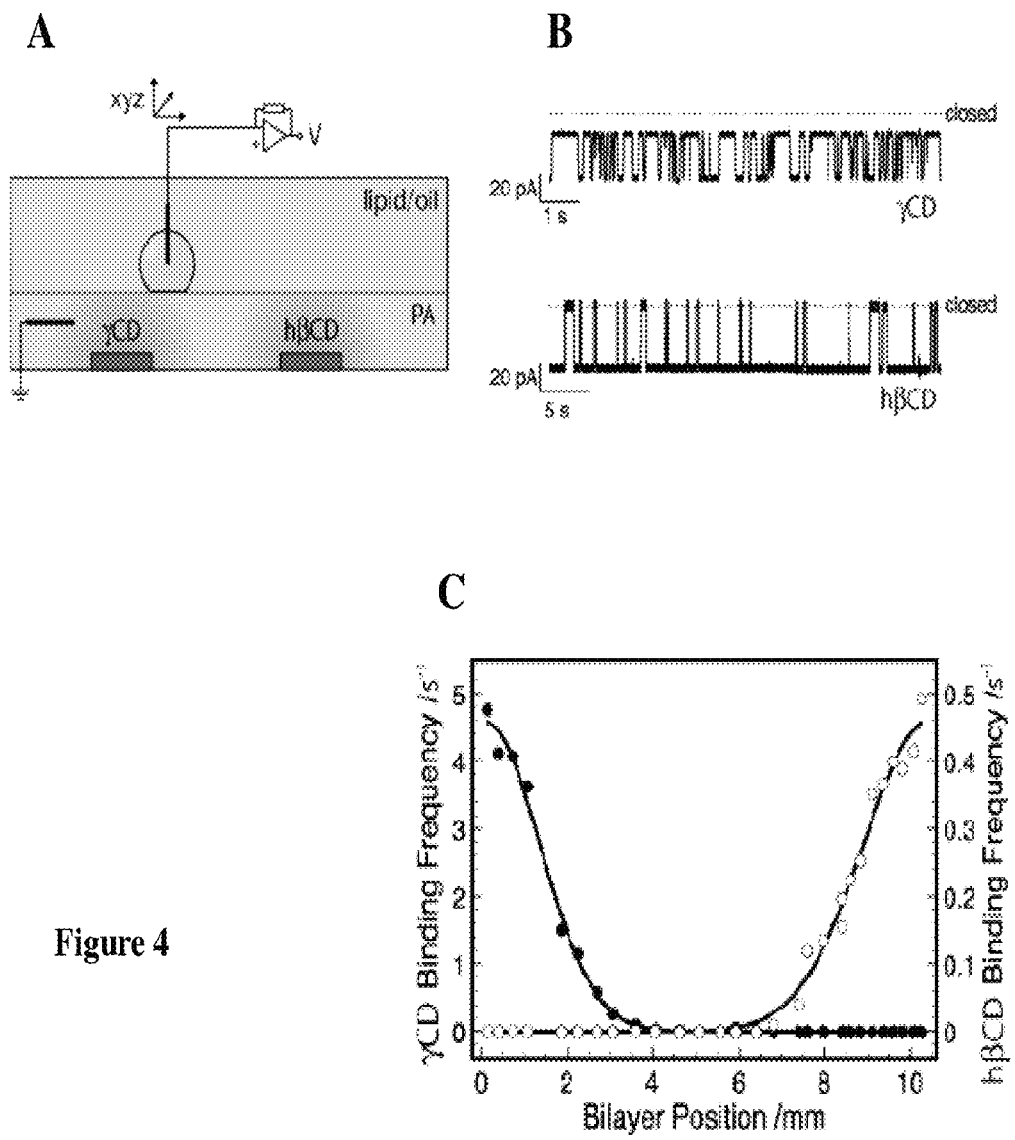
FIG. 4—illustrates scanning of cyclodextrins in gels using droplet-on-hydrated-support bilayers.

2% polyacrylamide gels were doped via absorption from blotted protein solution with approximately 10 µM of γ-cyclodextrin (γCD) and heptakis(2,3,6-tri-O-methyl)-β-cyclodextrin (hβCD) in two regions spaced approximately 10 mm apart (FIG. 4A). Following a 30 minute immersion in a DPhPC/$C_{16}$ solution, the gel was scanned between the two cyclodextrin regions with a 200 nL droplet containing αHL-WT. Under the experimental conditions γCD binding to αHL-WT produces a current block of 68%, and hβCD binding to αHL-WT produces a current block of 95%. These different binding amplitudes permit positive identification of both analytes with αHL-WT (FIG. 4B).

In this experiment the droplet was translated across the hydrogel without removing the lipid bilayer from the surface, retaining the αHL-WT channels in the lipid bilayer throughout the scan. The position of the lipid bilayer was recorded by imaging its position on an inverted microscope, and cyclodextrin binding events were observed electrically. Cyclodextrin binding frequency was determined by dividing the total number of events by the number of αHL-WT channels in the lipid bilayer. FIG. 4C shows the diffusion limited localised binding of the two cyclodextrin analytes, plotting γCD and hβCD binding frequency in a scan between the two regions.

Bilayer Production Using a Pipette

Figure 5:
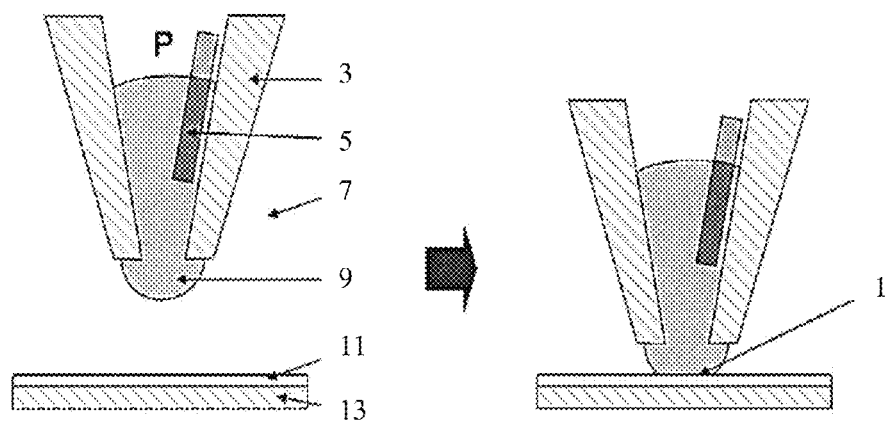
FIG. 5—shows a diagram of a droplet (hydrophilic body) ejected from a pipette tip, whilst immersed in a lipid/oil solution. The droplet is contacted with a hydrogel (hydrated support) to form a lipid bilayer.

With reference to FIG. 5, a hydrogel 11 is layered over a substrate 13 to form a hydrated support which is then immersed in a lipid/oil solution 7, such that a lipid monolayer forms on the upper surface of the hydrogel. An aqueous droplet 9 is partially ejected from a pipette tip 3 whilst the pipette tip 3 is immersed in a lipid/oil solution 7. A lipid monolayer forms on the surface of the droplet. The size of the droplet is controlled by how much of the aqueous solution is pushed out of the pipette tip on the application of pressure in the pipette. The size of the area of contact between the droplet and hydrogel will determine the length of the bilayer formed. The area of contact can be controlled by controlling the size of the droplet and the proximity of the pipette tip to the hydrogel.

The aqueous droplet 9 is contacted with the hydrogel 11 to form a lipid bilayer 1. A first electrode 5 in contact with the aqueous droplet 9 is used in conjunction with a second electrode (not shown) in contact with the hydrogel 11 to measure electrical activity across the lipid bilayer 1. The electrodes are Ag/AgCl.

By moving the pipette in the x/y plane the bilayer can be translocated across the surface of the hydrogel.

Figure 6:
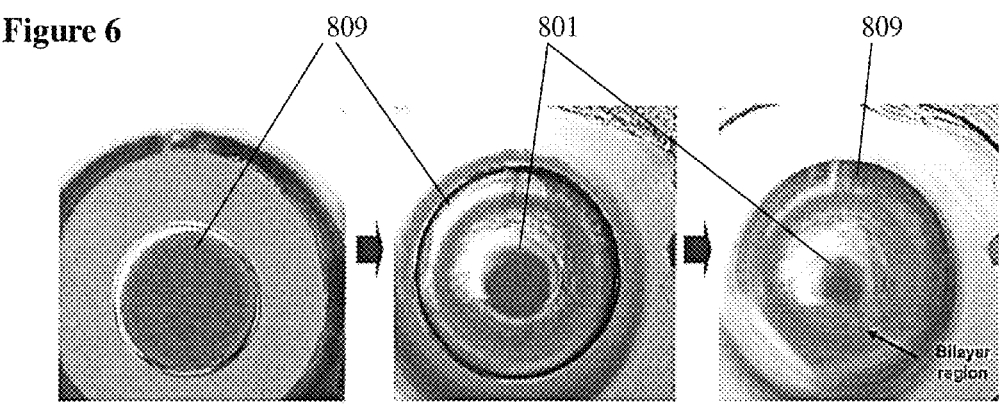
FIG. 6—illustrates a droplet-on-hydrated-support bilayer produced using the method of FIG. 5 visualised from below using an inverted microscope.

FIG. 6 uses inverted microscopy to visualise the formation of a lipid bilayer 801 between an aqueous droplet 809 and a transparent hydrated support (not shown) as the droplet and support are brought into contact.

Droplets in a Scanning 'Pipette'

Figure 7:
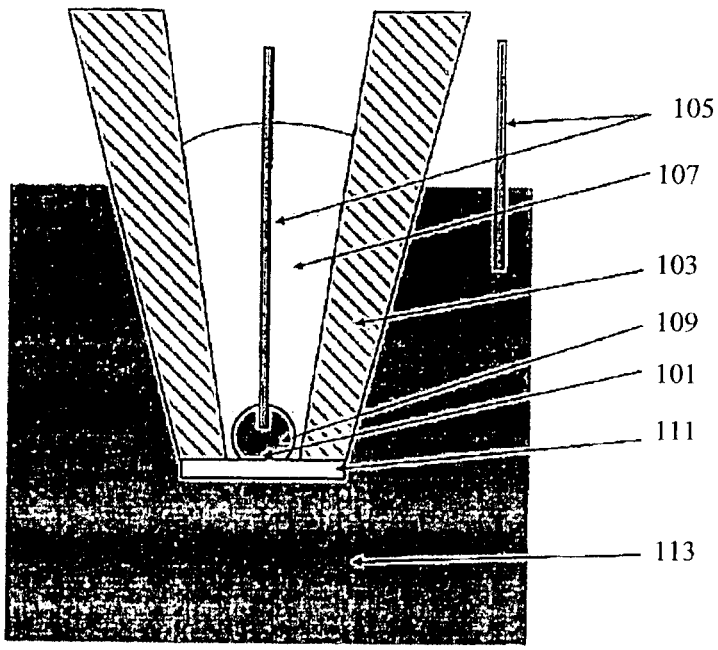
FIG. 7—shows a diagram of a lipid bilayer formed on a hydrated support fixed to a tip of a pipette which can be used to scan or probe an aqueous system.

FIG. 7 illustrates that droplet-on-hydrated-support bilayers can be formed on a hydrated supported mounted in a translatable scanning pipette tip. More specifically, a hydrated support 111 is fixed to the opening of a pipette tip 103, and the pipette tip is filled with a lipid/oil solution 107. An aqueous droplet 109 is immersed in the lipid/oil solution and contacted with the hydrated support 111 to form a lipid bilayer 101. The lipid bilayer 101 can be used to scan or probe an aqueous system 113 by immersing the pipette tip 103 into an aqueous system 113. A pair of electrodes 105 is provided to measure electrical activity across the lipid bilayer 101. One electrode 105 is in contact with the aqueous droplet 109 and the other electrode 105 is in contact with the aqueous system 113.

As long as the hydrated support is porous the bilayer can sense molecules in the aqueous system which can pass though the pores. The size of the pores in the support can be controlled to filter what material actually reaches the bilayer.

Alternative Device for the Production of a Bilayer

Figure 13A:
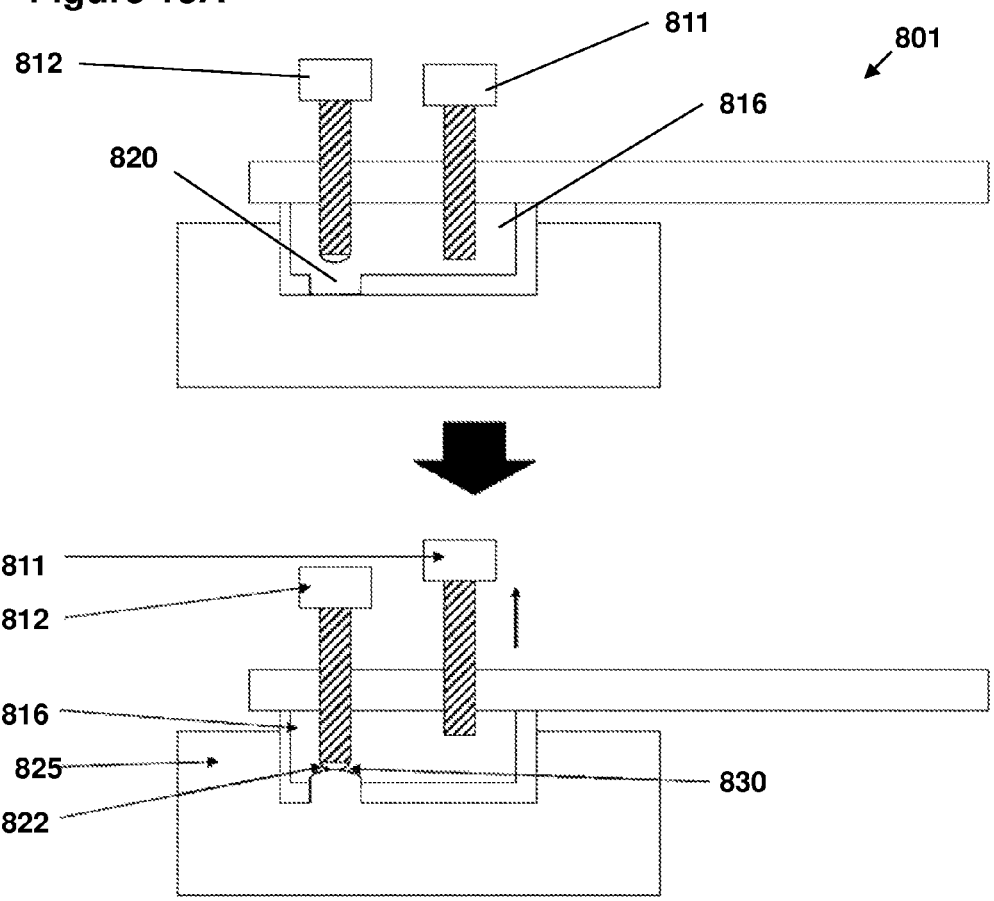
FIG. 13A—shows an alternative portable device for use in producing a bilayer according to the invention.

FIG. 13A illustrates an alternative portable device for producing a bilayer according to the invention. The device 801 is made of PMMA and comprises a first screw 811, a second screw 812, a chamber 816 and a hole 820.

In use, the chamber 816 is filled with oil and a droplet or agarose ball 822 is placed on the end of the second screw 812. The first screw 811 is adjustable to adjust the oil volume in the chamber 816. The second screw 812 is adjustable to adjust the height of the droplet or agarose ball 822.

To form a bilayer 830, the device 801, containing oil and including a droplet or agarose ball 822, is placed in a solution 825, the solution may be water. The first screw 811 is then raised to increase the volume in the chamber 816 which draws solution 825 into the chamber. When the solution 825 contacts the droplet or agarose ball 822 a bilayer 830 spontaneously forms. By adjusting the height of the second screw 812 the size of the bilayer 830 can be adjusted. By connecting the second screw 812 to an electrode, and placing a separate electrode in the solution 825, electrical access to the bilayer 830 is allowed. Furthermore, when the device 801 is removed from the solution 825 the device holds onto enough solution 825 to maintain the bilayer 830. This allows the bilayer to be removed from one solution and returned to a different solution.

Figure 13B:
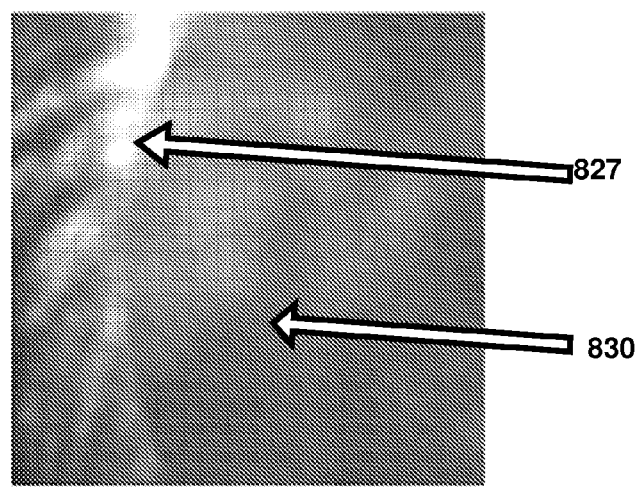
FIG. 13B—illustrates a bilayer produced using the device of FIG. 13A visualised from below using an inverted microscope.

FIG. 13B illustrates a bilayer 830 formed using the apparatus of FIG. 13A. The edge 829 of the bilayer 830 is clearly visible.

Device for Producing an Array of Bilayers

Figure 14A:
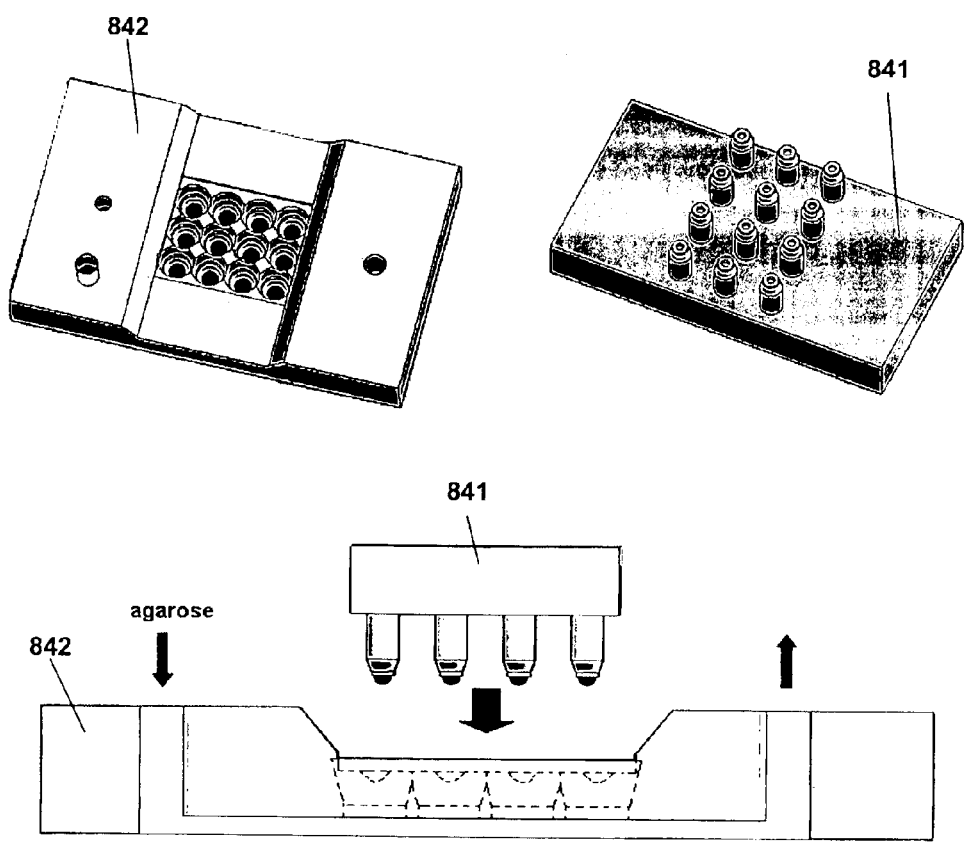
FIG. 14A—shows a device for producing an array of bilayers.
Figure 14B:
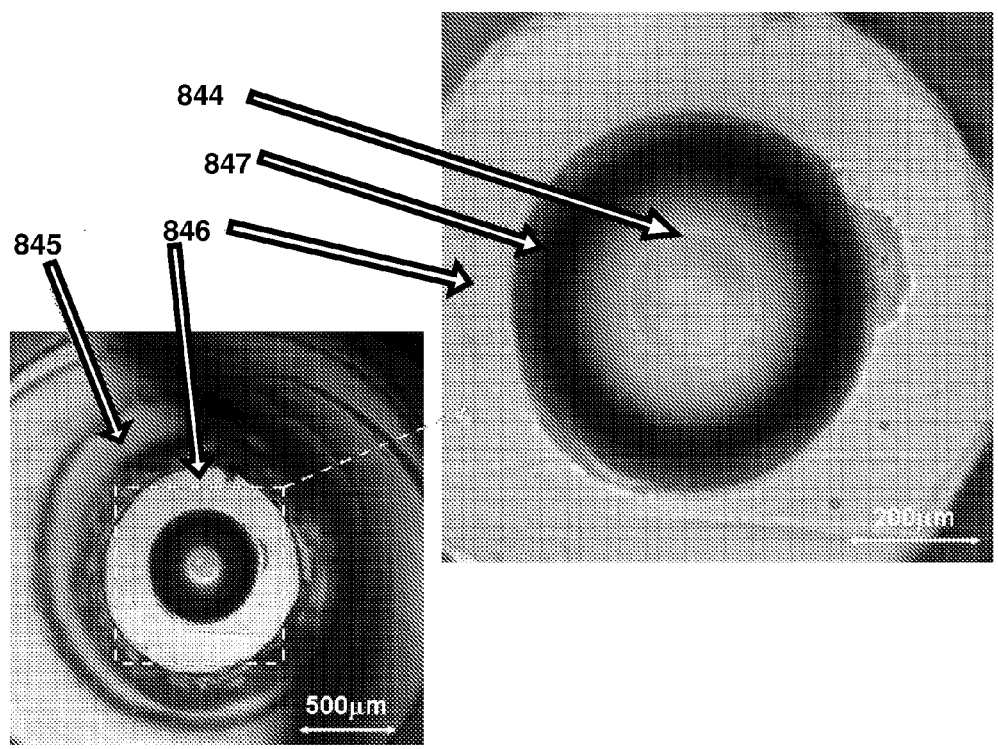
FIG. 14B—illustrates a bilayer produced using the device of FIG. 14A.

FIG. 14A depicts a device which can be used to produce an array of bilayers. The device comprises a base 842 and a lid 841. The base 840 is filled with agarose in the lower channel, then filled with a lipid/oil solution and left to equilibrate so that a monolayer forms on the agarose substrate. The lid 841 is dipped in a bulk aqueous solution, and through hydrophilic interaction with the plastic used to make the lid, small droplets remain on the lid. The lid is then lowered into the base, such that the droplets remain in oil for a time to equilibrate, before the lid is then lowered further to bring the droplets into contact with the underlying agarose. An array of bilayers then forms spontaneously where the droplets contact the agarose surface. By using electrodes connected to each of the droplets through the lid, and with a common electrode in the agarose, each bilayer in the array is individually accessible for electrical measurements. The nature of the device allows individual bilayers 844 to be imaged from below with a microscope, as can be seen in FIG. 14B, in which an agarose wall 845, a plastic support 846 and the suspended droplet 847 are also visible.

Device Capable of Perfusion of the Aqueous Phase

Figure 15A:
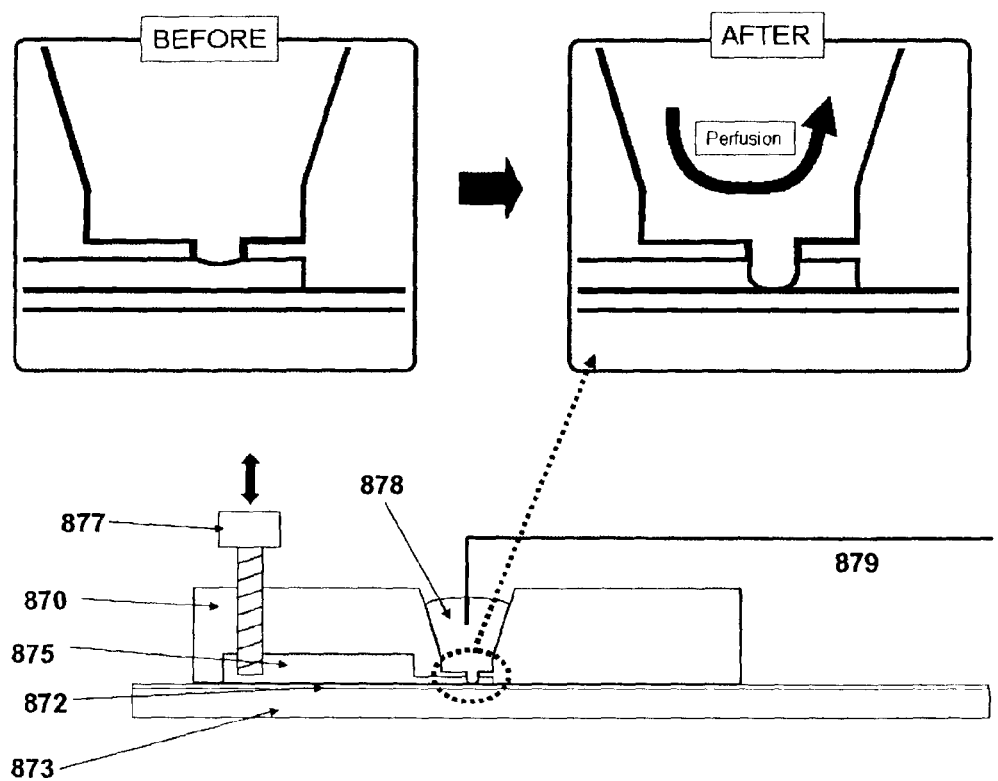
FIG. 15A—shows a device for producing a bilayer in which the aqueous phase is capable of perfusion.

FIG. 15A illustrates how a basic device to produce droplet-on-hydrated-support bilayers according to the invention can be extended to provide control of the volume of the oil phase (in this case with an adjustment screw) to manipulate the bulk liquid phase being drawn into the device.

In this embodiment a PMMA device 870 is attached to an underlying agarose layer 872 mounted on glass 873. An internal cavity 875, channel, or network of channels is filled with a lipid/oil solution. The internal oil-filled cavity 875 is open to the environment at one end, and terminates with a mechanism to control the oil volume at the other end, in this case a screw. When the screw is wound in or unwound, the oil is pushed into or pulled out of the cavity. The means of adjusting volume need not be a screw, and can extend to any means of controlling the volume of the oil, such as, it may be solid object such as a pin or needle pushed into the sample, which could be actuated by a stepper motor or syringe driver, for example. Alternatively, the volume in the cavity may be controlled by a syringe upstream, or by a microfluidic pump. Alternatively, the cavity itself, or parts of the cavity, could be made of a deformable material or include a membrane section, that when compressed adjusts the volume of the oil. When the oil is pulled into the cavity 875, bulk water or bulk aqueous volume 878 (added to the outside of the device) is also pulled into the cavity. Where the water/aqeuos volume contacts the underlying agarose a bilayer will spontaneously form.

Figure 15B:
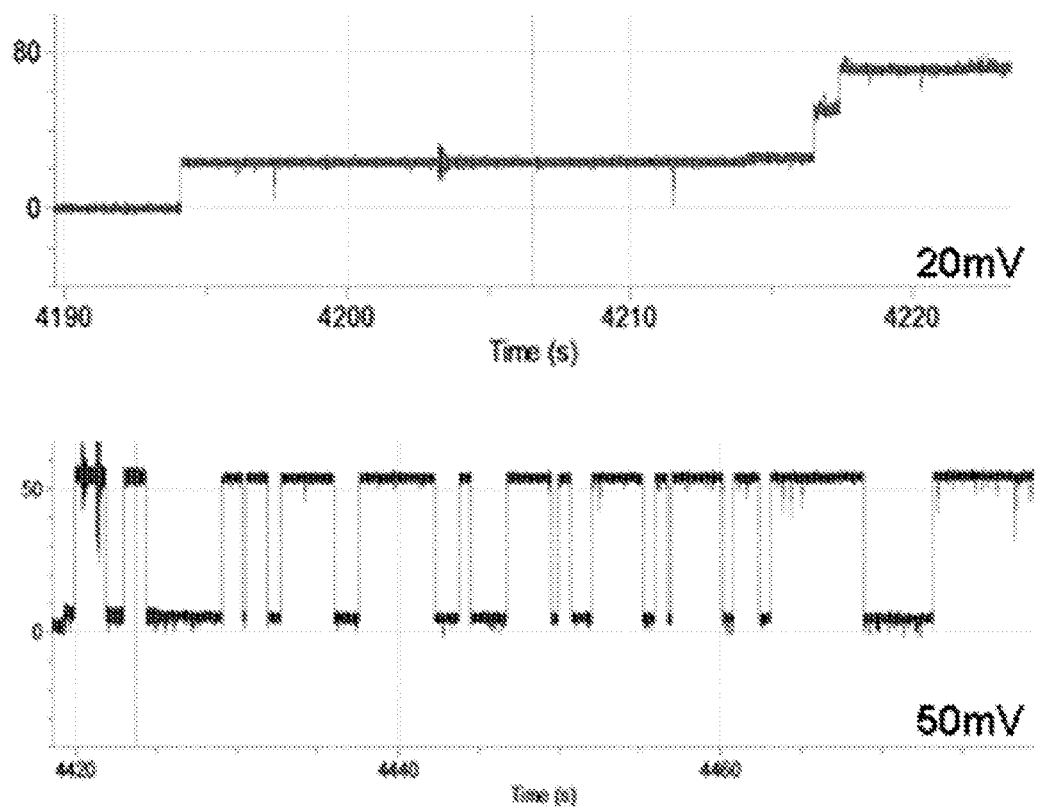
FIG. 15B—illustrates electrical traces produced using the device of FIG. 15A, in the top trace α-hemolysin channels are shown inserting into the bilayer, in the bottom trace cyclodextrins are shown binding.

With an electrode 879 in the bulk water or aqueous volume 878, and another electrode 872 in the agarose 872 the bilayers are accessible for electrical measurements. FIG. 15B illustrates an electrical trace produced using the device of FIG. 15A showing an example of α-hemolysin channels inserting into the bilayers (top), and binding cyclodextrins (bottom).

Figure 15C:
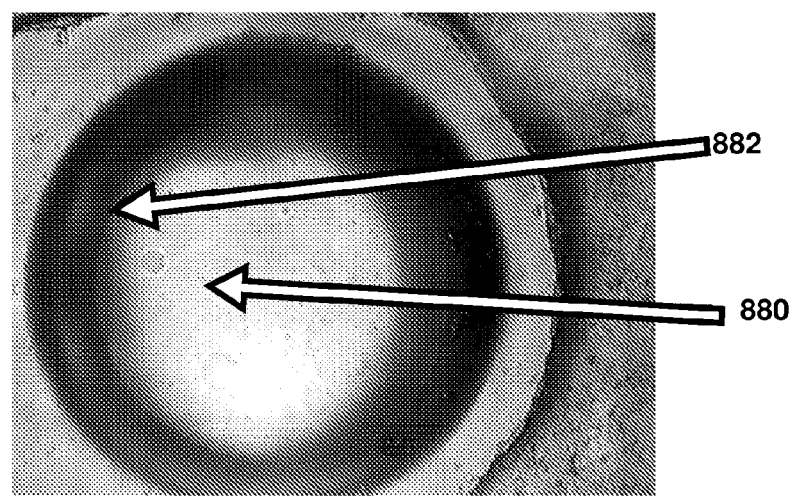
FIG. 15C—illustrates a bilayer produced by the device of FIG. 15A.

The bilayers can also be imaged using a microscope, see FIG. 15C, which show the bilayer 880 and the bilayer edge 882.

Figure 16:
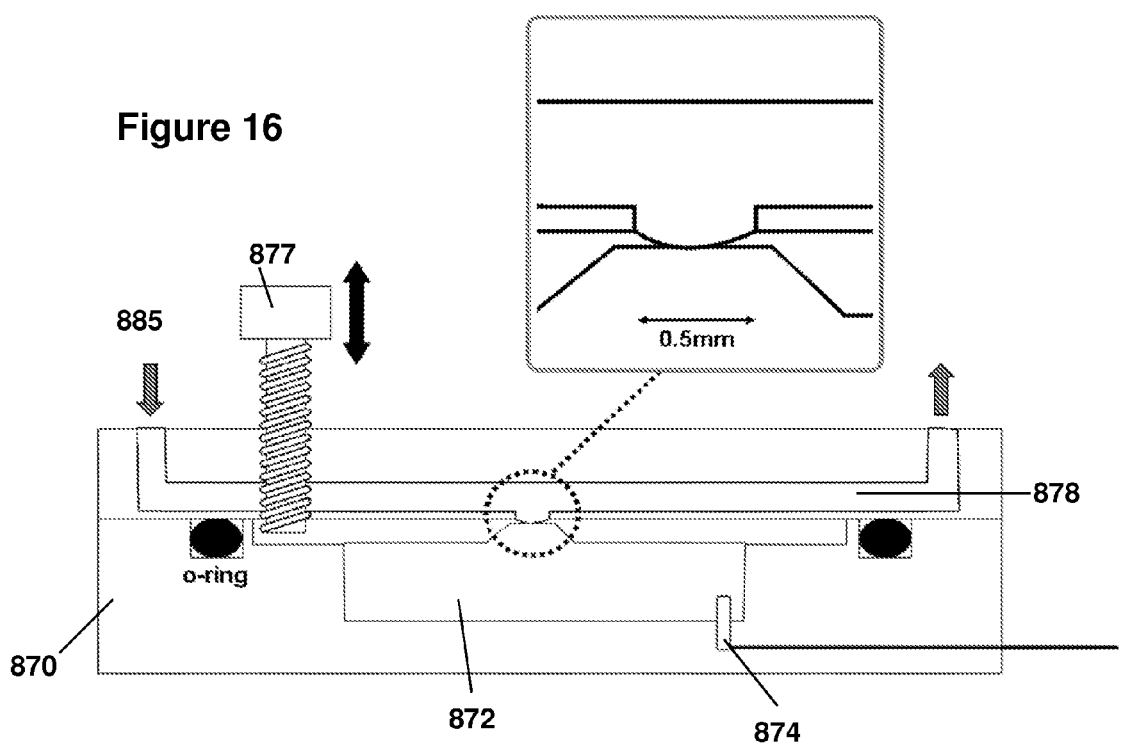
FIG. 16—shows an alternative device to that of FIG. 15A in which the bulk aqueous volume is a microfluidic channel.

The bulk aqueous volume in the device can be a microfluidic channel 885 as depicted in FIG. 16.

A device according to this embodiment, and illustrated in FIGS. 15A and 16, has the advantage that the bulk aqueous volume is open to the external environment which means that there is easier access for adding components to the system, which is difficult in a closed droplet system, and also that the volume can be perfused to fully exchange and alter the contents of the aqueous volume.

Control on Bilayer Area and Capacitance Measurements

Figure 8:
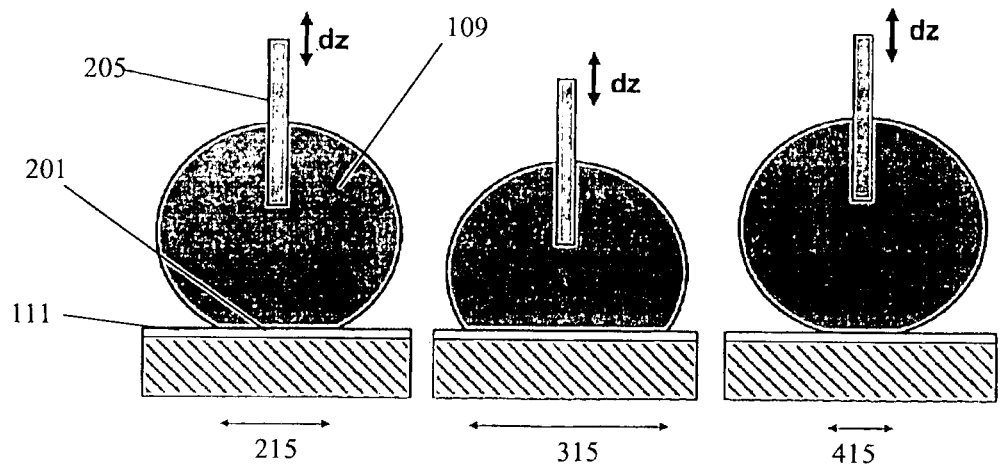
FIG. 8—shows a diagram of how the lipid bilayer can be increased and decreased in area by moving the centre of the aqueous droplet towards or away from the hydrated support using an electrode inserted in the droplet or in electrical contact with the droplet.

The droplet-on-hydrated-support bilayers subject of this application can be very large, greater than 1 cm, or very small, less than 1 micrometer. The area of the bilayer can be adjusted very quickly by adjusting the height of the droplet relative to the hydrated support. As is illustrated in FIG. 8, the size/area 215, 315, 415 of the lipid bilayer 201 can be increased or decreased by moving the centre of the aqueous droplet 109 towards or away from the hydrated support 111. In this example the droplet is moved by moving the electrode 205 in the droplet towards or away from the hydrated support 111.

By monitoring capacitance across the bilayer the area of the bilayer can be monitored. Bilayers formed by the method of the invention shows a linear response of bilayer to area to capacitance. This relationship is regardless of whether the bilayer has been reformed and what area changes the bilayer has been through.

The Production of Large Bilayers

By using devices such as those described herein, and the method of the invention, larger bilayers, of 1 mm, 1 cm or more, can be formed. For example, by using the oil withdrawing techniques discussed herein, bulk water can be drawn further and further down channels into the cavity of a device to produce a large bilayer.

Figure 17:
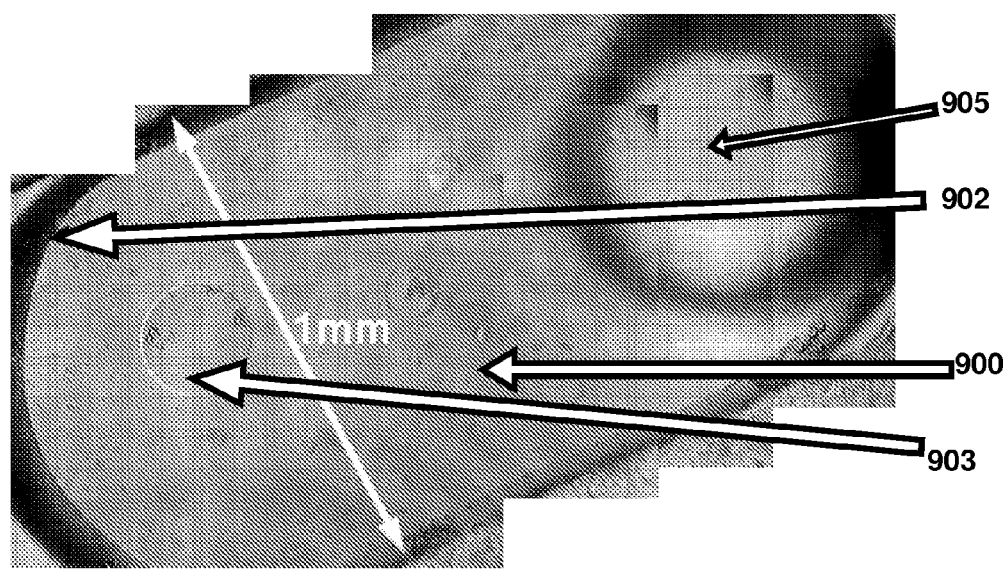
FIG. 17—illustrates a large bilayer produced by the method of the invention.

FIG. 17 shows a composite of images (the bilayer is too big to be observed in its entirety) taken on a microscope using the 10× objective in which the bilayer 900 is approximately 1 mm by 2 mm. The bilayer edge 902 is visible as are small oil inclusions 903 and the bulk water inlet 905.

Figure 18:
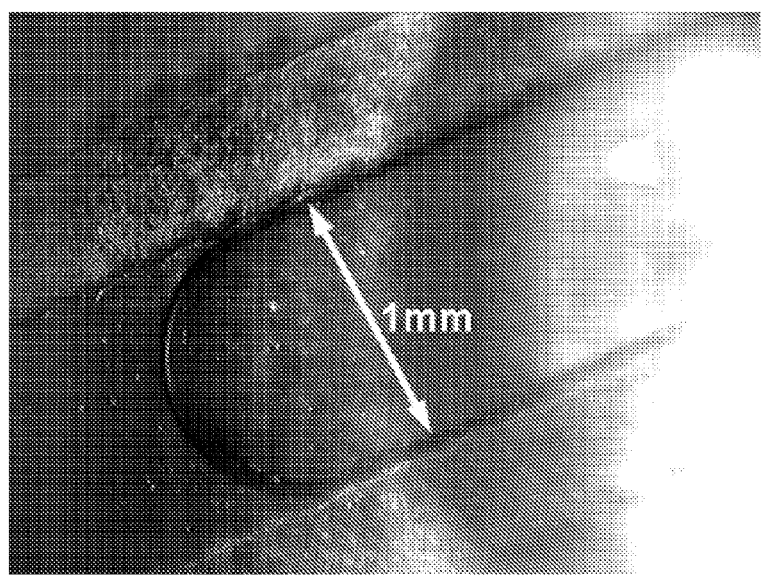
FIG. 18—illustrates a further large bilayer produced by the method of the invention.

FIG. 18 shows a slightly larger bilayer as the bilayer of FIG. 17 is pulled further into the channel, this bilayer is approximately 1 mm by 5 mm in size. Bilayers of 1 mm by 1 cm in size were also produced, and larger bilayers of many cms in size could be created. These larger bilayers may have a capacitance of ~100,000 pFarads or more for a DiPhytanoylPC bilayer. This is in comparison to artificial bilayers produced using previously known methods which are a few hundred micrometers in diameter, and which have capacitances of a few hundred pFarads for DiphytanoylPC bilayers.

Bursting, Injection and Perfusion of Droplet-on-hydrated-support Bilayers

Figure 9:
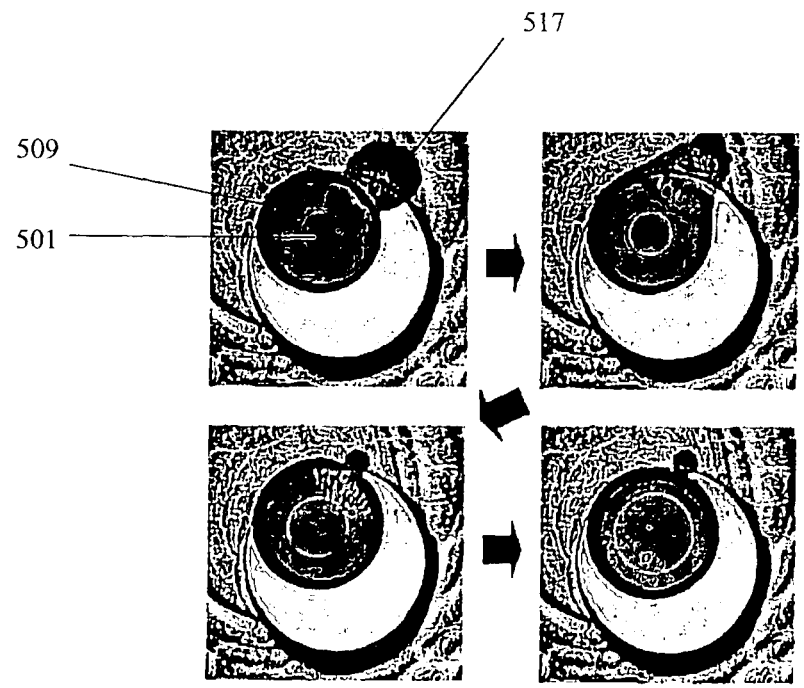
FIG. 9—illustrates how a second aqueous droplet carrying a cargo of reagents can be burst together with an aqueous droplet without rupturing the bilayer.

The droplet part of a droplet-on-hydrated-support bilayer can be burst without rupturing the bilayer. This is illustrated in FIG. 9 where the bursting of a cargo-carrying droplet into an existing droplet does not disrupt the bilayer. More specifically, a second aqueous droplet 517 carrying a cargo of reagents is shown bursting/fusing together with the existing aqueous droplet 509 without rupturing the bilayer 501.

Figure 10:
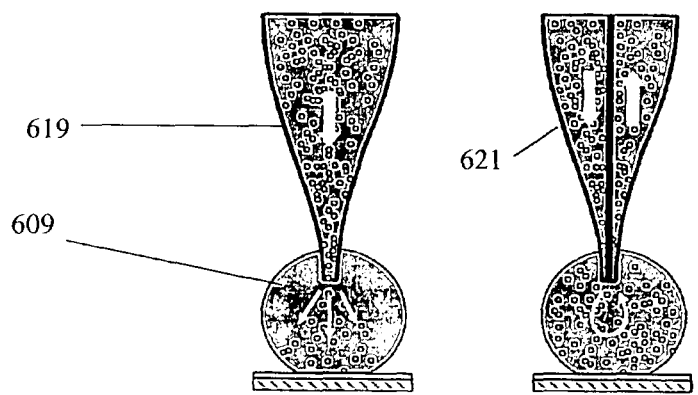
FIG. 10—shows a diagram of how reagents can be introduced into an aqueous droplet by injection from (A) a micro-pipette, or (B) a micro-pipette with a multi bore capillary.

FIG. 10 illustrates that reagents can be introduced into an aqueous droplet 609 by injection from a micro-pipette 619 or a micro-pipette with a multi bore capillary 621. This offers a simple way of introducing compounds into an existing droplet.

Droplet-on-hydrated-support Bilayers in Large Connected or Unconnected Networks

Multiple droplet-on-hydrated-support bilayers may be formed between individual unconnected droplets on a hydrated support or between multiple connected droplets on a hydrated support.

Figure 11:
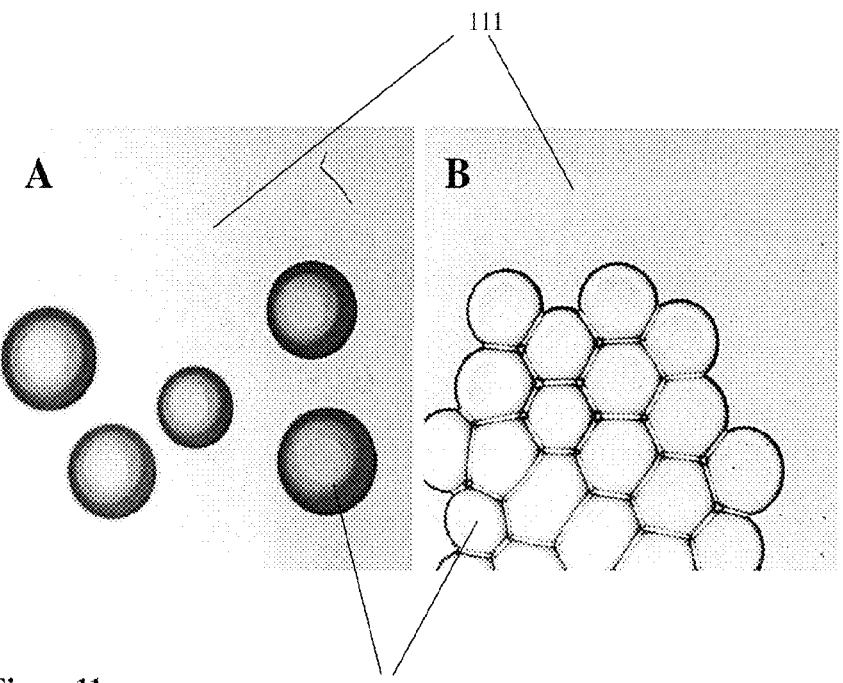
FIG. 11—illustrates multiple droplets-on-hydrated-support bilayers on a single hydrated support.

With reference to FIG. 11, multiple droplet-on-hydrated-support bilayers 709 are dispersed on a single hydrated support 111. FIG. 11A shows a plurality of independent/separate aqueous droplets 709 on the hydrated support 111 all of which are forming a bilayer with the support. FIG. 11B shows a plurality of aqueous droplets 709 connected in an array on the hydrated support 111, forming multiple bilayers between the droplets 709 and with the hydrated support 111.

Such large arrays are suitable for fluorescent experiments. These arrays may also be used for larger statistical studies. For example, an array of tiny droplets, from about 10 s of nanoliters to 10 s of picoliters, can be made with the probability tuned that each contains only one molecule of a given protein/reagent. Experiments can then be performed that track the turnover of an enzyme, for example, at the single molecule level.

Large arrays could also be used to fluorescently scan hydrogels containing isolated protein bands. For example if an array of droplets containing a Ca-sensitive fluorophore containing polymer is deposited over a gel containing calcium and isolated alpha-hemolysin channels in an electrophoretically focussed band, then droplets positioned over the protein band would insert the αHL and become fluorescent as calcium entered the droplets.

Droplet-on-hydrated-support Bilayers for Fluorescence

Droplet-on-hydrated-support bilayers laid down on thin hydrated supports can be fluorescently examined using total internal reflection fluorescence (TIRF) microscopy.

Figure 12:
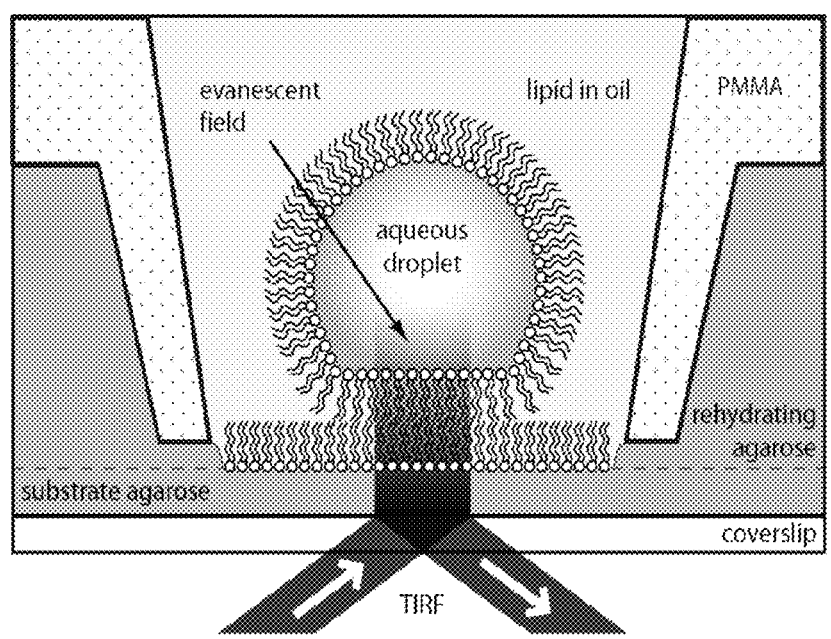
FIG. 12—illustrates total internal reflection fluorescence microscopy on a droplet-on-hydrated-support bilayer.

FIG. 12, which illustrates total internal reflection fluorescence microscopy on a droplet-on-hydrated-support bilayer, a supporting substrate comprised of a thin layer of agarose is formed on a glass coverslip. This thin substrate is rehydrated by filling a polymethyl methacrylate (PMMA) micro-channel device with aqueous agarose. The device wells are filled with a solution of lipid in oil. An aqueous droplet is placed on top of the hydrogel underneath the oil. A lipid bilayer forms at the interface between the two aqueous phases. The evanescent field propagates into the droplet-on-hydrated-support bilayer illuminating the lipid bilayer and fluorophore-tagged biomolecules in the droplet.

TIRF techniques may also be used in combination with other analysis techniques, for example, in combination with acquiring electrical data. The combination of data may provide improved information on protein function.

Efficiency of Bilayer Formation

Experiments in which the hydrophilic body was a water droplet, and a planar 1% agarose gel made with ultrapure water was the hydrated support, demonstrated that 20 water droplets all formed bilayers within 1 minute of contact between the water droplet and the agarose gel. The bilayers were observed to be intact after 2 weeks.

Concentration and Crystallisation of Membrane Proteins

Figure 19:
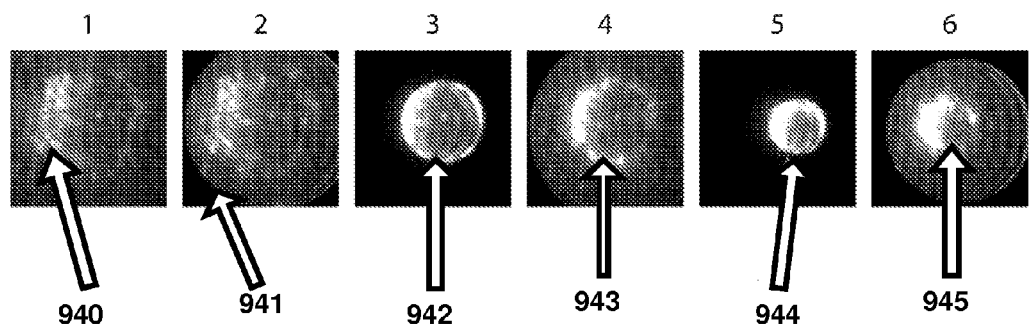
FIG. 19—illustrates the concentration of membrane bound proteins using a bilayer according to the invention.

FIG. 19 shows how bilayers according to the invention can be used to concentrate membrane proteins. This could be a means to produce 2-dimensional crystals or semi-ordered lattices of membrane proteins for further study. By inserting membrane proteins into a droplet-on-hydrogel bilayer, then shrinking the bilayer size by pulling the droplet perpendicularly from the surface, it is possible to drag membrane proteins inwards along the bilayer edge, without removing them from the bilayer. This results in a concentration of the inserted membrane proteins towards the centre of the bilayer.

FIG. 19 demonstrates the concentration of α-hemolysin pores embedded into a droplet-on-hydrogel bilayer. A 1% (w:v) thin agarose gel was deposited onto a coverslip and dehydrated, it was then rehydrated using a 1.5% (w:v) agarose containing buffer and 750 mM $CaCl_2$. A droplet containing the calcium indicator dye Fluo-4 (25 µM), α-hemolysin heptamers, 1.5M KCl and a buffer, was used to create a droplet-on-hydrogel bilayer on this thin agarose gel.

Bilayer fluorescence (afforded by the non-chelating Fluo-4) was imaged as a circular disc through TIRF illumination. Upon insertion of α-hemolysin pores into the bilayer, calcium flux into the droplet is possible. In this example the flux was enhanced by the application of an externally applied negative potential from electrodes inserted into the gel (ground) and droplet. This resulted in an enhanced fluorescence emanating from the vicinity of the pores (imaged as a spot). This was due to the fluorescence of the Fluo-4 near the pore greatly increasing in intensity upon its immediate chelation of calcium upon entry into the droplet.

FIG. 19 shows diffuse α-hemolysin pores (as fluorescent spots) 940 diffusing in the bilayer using the method described above. The bilayer is then gradually shrunk 941, resulting in the pores being condensed as they were dragged inwards by the encroaching bilayer edge 942. When the bilayer area was enlarged again 943, it was possible to see that the pores had been concentrated to where the bilayer edge was shrunk. Further concentration of the pores ensued 944 by repeating this process, leading to further condensation of the pores towards the centre of the bilayer area 945.

Discussion

Although droplet-on-hydrated-support bilayers represent a significant departure from conventional planar lipid bilayers, they are easier to prepare and work with, and are similarly amenable to single-channel recording examinations of both major classes of membrane protein. Droplet-on-hydrated-support bilayers are more stable than planar bilayers, and in contrast to the typical planar bilayer lifetime of a few hours (Miller, C. 1986. Plenum Press: New York), droplet-on-hydrated-support bilayers are often still functional several weeks after formation. This opens up avenues for long timescale experiments that have not been previously possible.

Droplet-on-hydrated-support bilayers also possess a number of other unique properties: (i) the lipid bilayers can be moved across the surface of a hydrated support. This has been exploited in hydrogel scanning experiments; (ii) droplet-on-hydrated-support bilayers provide reliable access to stable bilayers over a much great size range (<1 µm to >1 mm) than possible using alternative techniques; (iii) the area of the lipid bilayer can be adjusted during an experiment. For example, this may be used to control the number of inserted proteins in single-channel recording experiments; where the lipid bilayer is initially enlarged to increase the probability of protein insertion, then rapidly reduced once a single protein has inserted to minimise the chances of further insertions. Reducing the lipid bilayer area may also be used to concentrate transmembrane proteins inserted in a lipid bilayer. This may provide an alternative means to crystallise membrane-proteins, and for improving the probability of observing protein-protein interactions; and (iv) the lipid bilayer can be removed and reformed many times without mixing the droplet and hydrogel solutions. This may be used to reset single-channel recording experiments, as removing the lipid bilayer also appears to remove inserted transmembrane proteins. The fact that no contents mixing occurs is also important for experiments where cross-contamination is an issue.

The sensitivity of droplet-on-hydrated-support bilayer gel scanning allows direct study of low levels of endogenous protein from cell extracts without the need for over-expression. In contrast, examining proteins without over-expression using either traditional patchclamp techniques or planar lipid bilayers is difficult. Although whole-cell patch clamping can examine low levels of endogenous protein, it is often necessary to compensate for other constituents of the system due to the heterogeneous nature of cell membranes (Hamill, O. P. et al., 1981. *Pflugers Archiv-European Journal of Physiology* 391, 85-100; Ashley, R. H. 1995. IRL). It is possible to circumvent this problem using artificial lipid bilayers, however, it is difficult to extract and concentrate protein in sufficient quantities to successfully reconstitute in these bilayers (Miller, C. 1986. Plenum Press: New York; Ashley, R. H. 1995. *IRL*).

Droplet-on-hydrated-support bilayer gel scanning may be incorporated in existing proteomic methods that rely upon 2D gel electrophoresis to separate complex mixtures of cellular components for the discovery and characterisation of new proteins (Palzkill, T. 2002 *Proteomics*, Kluwer Academic Publishers, Boston, London; Simpson, R. J. 2003. *Proteins and proteomics: a laboratory manual*, Cold Spring Harbor Laboratory Press, Cold Spring Harbor, N.Y.). Droplet-on-hydrated-support bilayer gel scanning provides means to identify channel proteins in 2D gels. The observation that droplet-on-hydrated-support bilayer gel scanning does not appear to affect the proteins within the gel matrix means that repeated droplet-on-hydrated-support bilayer scanning of an individual gel under varying conditions, and subsequent analysis with conventional proteomic techniques (e.g. mass spectrometry) can be performed.

This invention provides a new platform for high-throughput studies of ion-channels. In particular, the requirement for only nanoliter volumes permits the application of many established emulsion-based technologies (Joanicot, M. & Ajdari, A. 2005. *Science* 309, 887-888; Ahn, K. et al., 2006. *Applied Physics Letters* 88; Link, D. R. et al., 2006. *Angewandte Chemie-International Edition* 45, 2556-2560; Hung, L. H. et al., 2006. *Lab on a Chip* 6, 174-178) for scaling-up and automating droplet-on-hydrated-support bilayers. For example, by combining flows of lipid/oil and water (Thorsen, T. et al., 2001. *Physical Review Letters* 86, 4163-4166) thousands of droplets with a controlled size can be created. Large numbers of droplet-on-hydrated-support bilayers may also be manipulated in an automated fashion with existing microfluidic techniques that can create and sort nanoliter droplets in oil (Ahn, K. et al., 2006. *Applied Physics Letters* 88; Link, D. R. et al., 2006. *Angewandte Chemie-International Edition* 45, 2556-2560).

The ability to image droplet-on-hydrated-support bilayers also allows the incorporation of fluorescence techniques. Single-channel recording experiments have provided a wealth of functional detail on many ion-channels, but it is difficult to link this to dynamic changes in protein structure. Single-molecule fluorescence of labelled proteins is one possible method of providing additional structural and dynamic information. Moreover, droplet-on-hydrated-support bilayers allows simultaneous optical and electrical measurements, which have the potential to uncover new aspects of channel function that cannot be elucidated with the individual techniques alone (Borisenko, V. et al., 2003. *Biophysical Journal* 84, 612-622; Ide, T. & Yanagida, T. 1999. *Biochemical and Biophysical Research Communications* 265, 595-599; Ide, T. et al., 2002. *Single Molecules* 3, 33-42; Macdonald, A. G. & Wraight, P. C. 1995. *Progress in Biophysics & Molecular Biology* 63, 1-29; Suzuki, H. et al., 2007. *Biosensors & Bioelectronics* 22, 1111-1115; Suzuki, H. et al., 2006. *Langmuir* 22, 1937-1942); for example, the dynamics of the folding and insertion of ion-channels.

Overall, the combination of enhanced stability, the ability to manipulate the lipid bilayer, electrical access, and imaging demonstrate that droplet-on-hydrated-support bilayers according to the invention provide a versatile platform for examining many aspects of membrane protein function.

The invention claimed is:

1. A method for producing a bilayer of amphipathic molecules comprising the steps of:
   (i) providing a hydrated support in a hydrophobic medium, wherein a first monolayer of amphipathic molecules is present on the surface of the hydrated support;
   (ii) providing a hydrophilic body in a hydrophobic medium, wherein a second monolayer of amphipathic molecules is present on the surface of the hydrophilic body; and
   (iii) bringing the first monolayer and the second monolayer into contact to form a bilayer of amphipathic molecules, wherein either: (a) the hydrophobic medium in which the hydrated support is provided contains amphipathic molecules and the hydrophobic medium in which the hydrophilic body is provided contains amphipathic molecules; or (b) the hydrated support contains amphipathic molecules and the hydrophilic body contains amphipathic molecules.

2. The method of claim 1 wherein the amphipathic molecules are lipid molecules.

3. The method of claim 2 wherein the lipid molecules are selected from the group consisting of fatty acyls, glycerolipids, glycerophospholipids, sphingolipids, sterol lipids, prenol lipids, saccharolipids, polyketides, phospholipids, glycolipids and cholesterol.

4. The method of claim 2 wherein the lipid molecule are selected from the group consisting of monoolein; 1,2-dioleoyl-sn-glyceron-3-phosphocholine (DOPC); 1,2-diphytanoyl-sn-glycero-3-phosphatidycholine (DPhPC); palmitoyl oleoyl phosphatidylcholine (POPC); 1-palmitoyl-2-oleoyl-phosphatidylethanolamine (POPE); 1-palmitoyl-2-oleoyl-phosphatidyethanolamine; and 1-palmitoyl-2-oleoylphosphatidylglycerol (POP E/POPG) mixture; and mixtures thereof.

5. The method of claim 1 wherein the hydrated support comprises a solid or a semi-solid substrate.

6. The method of claim 1 wherein the hydrated support is hydrophilic.

7. The method of claim 1 wherein the hydrated support is selected from the group consisting of hydrogels, agarose, polyacrylamide, [cross-linked] polyethylene glycol, nitrocellulose, polycarbonate, anodisc material, polyethersulphone, cellulose acetate, nylon, Naphion materials, mesoporous silica, water and glass.

8. The method of claim 1 wherein the hydrated support is a protein or analyte separation gel.

9. The method of claim 1 wherein the hydrophilic body comprises a droplet of aqueous solution.

10. The method of claim 9 wherein the droplet is from 5 nm to 10 cm in diameter.

11. The method of claim 1 wherein the hydrophilic body comprises a hydrated solid or semi-solid support/substrate.

12. The method of claim 1 wherein the hydrophobic medium is an oil.

13. The method of claim 12 wherein the oil is a hydrocarbon.

14. The method of claim 12 wherein the oil is selected from the group consisting of alkanes, alkenes, fluorinated oils, silicone based oils and carbon tetrachloride.

15. The method of claim 1 wherein the bilayer has a diameter from about 1 μ to greater than about 1 cm.

16. The method of claim 1 wherein a membrane-associated protein is present (a) in at least one of the hydrated support, the hydrophilic body and the hydrophobic medium, said membrane-associated protein being capable of insertion into the bilayer; or (b) in the bilayer.

17. The method of claim 16 wherein the membrane-associated protein is selected from the group consisting of a selective or non-selective membrane transport protein, an ion channel, a pore forming protein and a membrane-resident receptor.

18. The method of claim 16 wherein the one or more protein is inserted into the bilayer after the bilayer has formed.

19. The method of claim 1 wherein the area of the bilayer can be varied by varying the relative positions of the hydrophilic body and the hydrated substrate.

20. The method of claim 1 wherein the bilayer can be disassembled by removing contact between the hydrated support and the hydrophilic body.

21. The method of claim 20 wherein the bilayer can be reformed by restoring contact between a lipid monolayer on the hydrated support and a lipid monolayer on the hydrophilic body.

* * * * *